(12) United States Patent
Herdt et al.

(10) Patent No.: US 8,933,263 B2
(45) Date of Patent: *Jan. 13, 2015

(54) WATER TEMPERATURE AS A MEANS OF CONTROLLING KINETICS OF ONSITE GENERATED PERACIDS

(75) Inventors: Brandon Herdt, Hastings, MN (US); Richard Staub, Lakeville, MN (US); Thomas C. Rustad, Minneapolis, MN (US); Junzhong Li, Apple Valley, MN (US); David D. McSherry, St. Paul, MN (US); Paul R. Kraus, Apple Valley, MN (US); Richard Walsh, Woodbury, MN (US)

(73) Assignee: Ecolab USA Inc., Saint Paul, MN (US)

( * ) Notice: Subject to any disclaimer, the term of this patent is extended or adjusted under 35 U.S.C. 154(b) by 216 days.

This patent is subject to a terminal disclaimer.

(21) Appl. No.: 13/331,385

(22) Filed: Dec. 20, 2011

(65) Prior Publication Data

US 2012/0171076 A1    Jul. 5, 2012

Related U.S. Application Data

(60) Provisional application No. 61/427,951, filed on Dec. 29, 2010.

(51) Int. Cl.
| | |
|---|---|
| C07C 409/24 | (2006.01) |
| C07C 407/00 | (2006.01) |
| A01N 37/16 | (2006.01) |
| A01N 59/00 | (2006.01) |
| B01J 19/00 | (2006.01) |
| B01J 4/00 | (2006.01) |
| C02F 1/50 | (2006.01) |
| C02F 103/08 | (2006.01) |

(52) U.S. Cl.
CPC .............. *C07C 407/00* (2013.01); *A01N 37/16* (2013.01); *A01N 59/00* (2013.01); *B01J 19/0013* (2013.01); *B01J 4/008* (2013.01); *C02F 1/50* (2013.01); *C02F 2103/08* (2013.01); *B01J 2219/00121* (2013.01); *B01J 2219/00159* (2013.01)
USPC ........................................................... 562/6

(58) Field of Classification Search
CPC .............. C07C 407/00; C07C 409/24–409/26
See application file for complete search history.

(56) References Cited

U.S. PATENT DOCUMENTS

| | | | |
|---|---|---|---|
| 2,955,905 A | 10/1960 | Davies et al. | |
| 3,256,198 A | 6/1966 | Matzner | |
| 3,272,750 A | 9/1966 | Chase | |
| 3,432,546 A | 3/1969 | Oringer et al. | |
| 3,847,830 A | 11/1974 | Williams et al. | |
| 3,925,234 A | 12/1975 | Hachmann et al. | |
| 4,003,841 A | 1/1977 | Hachmann et al. | |
| 4,051,058 A | 9/1977 | Böwing et al. | |
| 4,126,573 A | 11/1978 | Johnston | |
| 4,170,453 A | 10/1979 | Kitko | |
| 4,233,235 A | 11/1980 | Camden et al. | |
| 4,370,251 A | 1/1983 | Liao et al. | |
| 4,412,934 A | 11/1983 | Chung et al. | |
| 4,483,778 A | 11/1984 | Thompson et al. | |
| 4,486,327 A | 12/1984 | Murphy et al. | |
| 4,617,090 A | 10/1986 | Chum et al. | |
| 4,655,781 A | 4/1987 | Hsieh et al. | |
| 4,778,618 A | 10/1988 | Fong et al. | |
| 4,964,870 A | 10/1990 | Fong et al. | |
| 5,030,240 A | 7/1991 | Wiersema et al. | |
| 5,122,538 A | 6/1992 | Lokkesmoe et al. | |
| 5,143,641 A | 9/1992 | Nunn | |
| 5,200,189 A | 4/1993 | Oakes et al. | |
| 5,314,687 A | 5/1994 | Oakes et al. | |
| 5,431,849 A | 7/1995 | Damhus et al. | |
| 5,503,765 A | 4/1996 | Schepers et al. | |
| 5,505,740 A | 4/1996 | Kong et al. | |
| 5,637,755 A | 6/1997 | Nagumo et al. | |
| 5,716,923 A | 2/1998 | MacBeath | |
| 5,718,910 A | 2/1998 | Oakes et al. | |
| 5,827,447 A | 10/1998 | Tamura et al. | |
| 5,827,808 A | 10/1998 | Appleby et al. | |

(Continued)

FOREIGN PATENT DOCUMENTS

| | | | |
|---|---|---|---|
| EP | 0267047 A2 | 5/1988 | |
| EP | 0269435 A2 | 6/1988 | |

(Continued)

OTHER PUBLICATIONS

International Search Report, completed and mailed on Jul. 31, 2012, Application No. PCT/IB2011/005834 filed on Dec. 20, 2011, Applicant: Ecolab USA Inc. et al. (9 pages).
Dannacher, Josef J., "Catalytic bleach: Most valuable applications for smart oxidation chemistry", Journal of Molecular Catalysis A: Chemical 251 (2006) 159-176.
Rusch gen. Klaas, Mark et al., "Biocatalytic peroxy acid formation for disinfection", Journal of Molecular Catalysis B: Enzymatic 19-20 (2002) 499-505.

(Continued)

*Primary Examiner* — Karl J Puttlitz
(74) *Attorney, Agent, or Firm* — McKee, Voorhees & Sease

(57) ABSTRACT

Methods and systems for temperature-controlled, on-site generation of peracids, namely peroxycarboxylic acids and peroxycarboxylic acid forming compositions are disclosed. In particular, methods for using an adjustable biocide formulator or generator system overcome the limitations of temperature on the kinetics of the peracid generation and/or peracid decomposition inside an adjustable biocide formulator or generator system. The methods include the controlling of the temperature of at least one raw starting material, namely water, to improve upon methods of on-site generation of peracids. The methods allow for the generation of user-selected chemistry without regard to the ambient temperatures of the raw starting materials and/or the biocide formulator or generator system.

11 Claims, 6 Drawing Sheets

(56) References Cited

U.S. PATENT DOCUMENTS

| | | |
|---|---|---|
| 5,977,403 A | 11/1999 | Byers |
| 5,998,350 A | 12/1999 | Burns et al. |
| 6,022,381 A | 2/2000 | Dias et al. |
| 6,177,393 B1 | 1/2001 | McGregor et al. |
| 6,207,632 B1 | 3/2001 | Brooker et al. |
| 6,221,341 B1 | 4/2001 | Montgomery |
| 6,399,564 B1 | 6/2002 | Speed et al. |
| 6,569,286 B1 | 5/2003 | Withenshaw et al. |
| 6,599,871 B2 | 7/2003 | Smith |
| 6,602,845 B2 | 8/2003 | Connor et al. |
| 6,649,140 B2 | 11/2003 | Paparatto et al. |
| 6,689,732 B1 | 2/2004 | Guedira et al. |
| 7,012,154 B2 | 3/2006 | Vineyard et al. |
| 7,547,421 B2 * | 6/2009 | McSherry et al. ............ 422/424 |
| 7,569,232 B2 | 8/2009 | Man et al. |
| 7,598,218 B2 | 10/2009 | Stolte et al. |
| 7,915,445 B2 | 3/2011 | Maatta et al. |
| 7,919,122 B2 | 4/2011 | Okano et al. |
| 8,075,857 B2 | 12/2011 | McSherry et al. |
| 2003/0100469 A1 | 5/2003 | Connor et al. |
| 2005/0008526 A1 | 1/2005 | Bianchetti et al. |
| 2006/0173209 A1 | 8/2006 | Vineyard et al. |
| 2007/0274857 A1 | 11/2007 | Okano et al. |
| 2008/0176784 A1 | 7/2008 | Clowes et al. |
| 2009/0018049 A1 | 1/2009 | Stolte et al. |
| 2009/0208365 A1 | 8/2009 | McSherry et al. |
| 2010/0084603 A1 | 4/2010 | Narayan et al. |
| 2011/0168567 A1 | 7/2011 | Smith et al. |
| 2011/0169270 A1 | 7/2011 | Todorof |
| 2011/0171062 A1 | 7/2011 | Wolfe |
| 2011/0173897 A1 | 7/2011 | Schneider |
| 2011/0177145 A1 | 7/2011 | Erkenbrecher, Jr. et al. |
| 2012/0172437 A1 | 7/2012 | Kraus et al. |

FOREIGN PATENT DOCUMENTS

| | | |
|---|---|---|
| JP | 62155203 A | 7/1987 |
| JP | 5186989 | 7/1993 |
| JP | 6305920 | 11/1994 |
| WO | 9115474 A1 | 10/1991 |
| WO | 9403395 A1 | 2/1994 |
| WO | 9424869 A1 | 11/1994 |
| WO | 9614384 A1 | 5/1996 |
| WO | 9616148 A1 | 5/1996 |
| WO | 9803513 A1 | 1/1998 |
| WO | 9931215 A1 | 6/1999 |
| WO | 2010050634 A1 | 5/2010 |

OTHER PUBLICATIONS

Rusch gen. Klaas, Mark et al., "Lipase-catalyzed conversions of trimethylsilyl ethers: deprotection, acetylation, epoxidation and one-pot-multi-step reactions", Journal of Molecular Catalysis B: Enzymatic 7 (1999) 283-289.

Tsunokawa, Youko et al., "A Versatile Method for Preparation of O-Alkylperoxycarbonic Acids: Epoxidation with Alkyloxycarbonylimidazoles and Hydrogen Peroxide", Tetrahedron Letters, vol. 23, No. 20, (1982), pp. 2113-2116.

Yin, De Lu (Tyler), et al., "Switching Catalysis from Hydrolysis to Perhydrolysis in *Pseudomonas fluorescens* Esterase", Biochemistry, (2010), 49, 1931-1942.

English Abstract of JP62155203, published on Jul. 10, 1987 (1 page).

English Abstract of JP6305920, published on Nov. 1, 1994 (1 page).

Caboni-Oerlemans, Chiara, et al., "Hydrolase-catalysed synthesis of peroxycarboxylic acids: Biocatalytic promiscuity for practical applications", Elsevier, Journal of Biotechnology, 126 (2006) 140-151 (12 pages).

Effkemann, Stefan, et al., "Peroxide analysis in laundry detergents using liquid chrornotography", Elsevier, Analytica Chimica Acta, 363 (1998) 97-103 (7 pages).

Leveneur, Sébastien, "Synthesis of peroxypropionic acid from propionic acid and hydrogen peroxide over heterogeneous catalysts", Elsevier, Chemical Engineering Journal, 147 (2009) 323-329 (7 pages).

Maeda, Hatsuo, et al., "Assessment of Acyl Groups and Reaction Conditions in the Competition between Perhydrolysis and Hydrolysis of Acyl Resorufins for Developing an Indicator Reaction for Fluorometric Analysis of Hydrogen Peroxide", Pharmaceutical Society of Japan, Cehm. Pharm. Bull. 50(2) 169-174, 2002 (6 pages).

Muurinene, Esa, "Organosolv Pulping—A review and distillation study related to peroxyacid pulping", Department of Process Engineering, University of Oulu, May 16, 2000, Oulu, Finland (314 pages).

Ogata, Y., et al., "The Formation of Peracids by the Perhydrolysis With Alkaline Hydrogen Peroxide", Tetrochem, vol. 23, pp. 3327-3332, Pergamom Press, 1967 (7 pages).

Rusch gen. Klaas, Mark, et al., "Lipase-catalyzed preparation of peroxy acids and their use for expoxidation", Elsevier, Journal of Molecular Catalysis A: Chemical 117 (1997) 311-319 (9 pages).

* cited by examiner

US 8,933,263 B2

WATER TEMPERATURE AS A MEANS OF CONTROLLING KINETICS OF ONSITE GENERATED PERACIDS

CROSS-REFERENCE TO RELATED APPLICATIONS

This application is a continuation-in-part of U.S. patent application Ser. No. 61/427,951, entitled Sugar Ester Peracid On-Site Generator and Formulator. The entire contents of this patent application are hereby expressly incorporated herein by reference including, without limitation, the specification, claims, and abstract, as well as any figures, tables, or drawings thereof.

This application is related to U.S. patent application Ser. Nos. 61/427,965, 13/331,304, now issued U.S. Pat. No. 8,846,107, and Ser. No. 13/331,486, entitled In Situ Generation of Peroxycarboxylic Acids at Alkaline pH and Methods of Use Thereof, U.S. patent application Ser. No. 13/330,915, entitled Sugar Ester Peracid On-Site Generator and Formulator, U.S. patent application Ser. No. 13/331,104, now issued U.S. Pat. No. 8,729,296, entitled Generation of Peroxycarboxylic Acids at Alkaline pH, and Their Use as Textile Bleaching and Antimicrobial Agents, U.S. patent application Ser. No. 13/330,981, now issued U.S. Pat. No. 8,858,895, entitled Continuous On-Line Adjustable Disinfectant/Sanitizer/Bleach Generator, each filed concurrently herewith. The entire contents of these patent applications are hereby expressly incorporated herein by reference including, without limitation, the specification, claims, and abstract, as well as any figures, tables, or drawings thereof.

FIELD OF THE INVENTION

The invention relates to methods and systems for temperature-controlled on-site generation of peracids, namely peroxycarboxylic acids and peroxycarboxylic acid forming compositions for use as oxidizing agents. In particular, methods for using an adjustable biocide formulator or generator system are provided for on-site generation of peroxycarboxylic acids and peroxycarboxylic acid forming compositions from at least one sugar ester. Methods of use overcome the limitations of temperature on the kinetics of the peracid generation. In particular, the present invention overcomes the limitation of temperature on the kinetics of both peracid production as well as the kinetics of peracid decomposition inside an adjustable biocide formulator or generator system.

BACKGROUND OF THE INVENTION

Peracids, also known as peroxyacids, are known for use as sanitizers, disinfectants, deodorizers, and bleaching agents, among other uses. Peroxycarboxylic acids in particular are known for use as antimicrobials and bleaching agents. Peracids such as peroxycarboxylic acid have known chemical disadvantages, namely, they are relatively instable in solution and decompose to ordinary oxyacids and oxygen. Conventional peroxycarboxylic acid compositions are made through an acid catalyzed equilibrium reaction. Most often, the peroxycarboxylic acids are generated in a chemical plant, and then shipped to customers for on-site use. Due to the limited storage stability of peroxycarboxylic acids they are often packed in special containers and shipped under the strict Department of Transportation (DOT) guidelines. Certain improvements to peroxycarboxylic acid stability have proved advantageous for shipping purposes, as described in U.S. patent application Ser. No. 11/847,604, entitled "Shelf Stable, Reduced Corrosion, Ready to Use Peroxycarboxylic Acid Antimicrobial Compositions," the entire contents of which are hereby expressly incorporated herein by reference.

Most commercially available products in an equilibrium mixture contain excess hydrogen peroxide in the presence of stabilizers and acid catalysts, to stabilize and improve the composition's shelf life. Despite such stability improvements, excess amounts of reagents (e.g., acids, oxidizing agents, and stabilizers) must be present in the compositions during shipping to prevent decomposition. Peroxycarboxylic acid instability, specifically limited storage stability, is described in detail in U.S. Pat. No. 8,034,759, entitled "Enhanced Stability Peracid Compositions," the entire contents of which are hereby expressly incorporated herein by reference.

Peracid generation is limited according to various kinetic reactions, including the temperature of the reaction. As a result, the generation of a peracid chemistry using the conventional acid catalyzed equilibrium reactions presents additional difficulties. In particular, changes in the ambient temperature of a location of a generator and/or of a raw starting material are expected to negatively impact the generation of peracid chemistry.

Accordingly, it is an objective of the claimed invention to develop methods and systems for on-site generation of peracids, including peroxycarboxylic acid generating compositions and peroxycarboxylic acids that are temperature insensitive.

A further object of the invention is to develop a system for generation of individual or mixed peracid chemistries according to user- or system-specific needs that may be generated in any on-site location regardless of ambient temperature conditions.

BRIEF SUMMARY OF THE INVENTION

An advantage of the invention is a system and methods for on-site generation of a biocide or antimicrobial agent. The system may be formulated into a number of designs, including for example, a mobile cart or generator that is particularly suitable for the on-site generation of peracid chemistries required in batch formulations and/or continuously generated formulations. It is a particular advantage of the present invention that peracid chemistries, including peroxycarboxylic acid forming compositions or peroxycarboxylic acids are generated on-site according to particular needs of a user or system to provide desired performance against particular organisms, as well as providing desired volumes of the same chemistry. In addition, the on-site generation is insensitive to the ambient temperatures of both the location of the system and the reagents utilized within the system. These benefits of the present invention ensure consistent generation of the peracid chemistries.

In an embodiment, the present invention is a method for on-site, temperature controlled peroxycarboxylic acid forming composition generation or peroxycarboxylic acid generation comprising: inputting a user-desired or system-controlled peroxycarboxylic acid forming composition or peroxycarboxylic acid formulation into a control software for on-site generation, wherein said input formulation selects an individual or mixed peroxycarboxylic acid forming composition or peroxycarboxylic acid and corresponding volume or mass for on-site generation; and combining one or more sugar esters of a polyhydric alcohol and a C1 to C18 carboxylic acid, a source of alkalinity and an oxidizing agent at alkaline pH in an adjustable biocide formulator or generator system at a pH above at least 12, wherein said system is an apparatus that is insensitive to environmental temperatures of the location of the apparatus and/or reagents comprising a reaction vessel, a series of feed pumps, an outlet for dosing a peroxycarboxylic acid forming composition from said reaction vessel and a controller for a user- or system-inputted selection device; and generating a peroxycarboxylic acid forming composition or peroxycarboxylic acid formulation; wherein said temperature insensitivity to the environmental temperatures of the location of the apparatus and/or reagents is controlled by a mechanism for maintaining a controlled temperature of said reaction vessel and/or one or more reagents; wherein said feed pumps are in fluid connection with said reaction vessel and supply one or more reagents to produce said peroxycarboxylic acid forming composition in said reaction vessel; and wherein said reaction vessel is in fluid connection with said outlet to dispense said peroxycarboxylic acid forming composition.

In a further embodiment, the present invention is a temperature controlled adjustable biocide formulator or generator system for on-site peroxycarboxylic acid forming composition generation comprising: an apparatus for producing peroxycarboxylic acid forming composition that is insensitive to environmental temperatures of the location of the apparatus and/or reagents comprising a reaction vessel, a series of feed pumps, an outlet for dosing a peroxycarboxylic acid forming composition from said reaction vessel and a controller for a user- or system-inputted selection device; a temperature controlled mechanism for maintaining a controlled temperature of said reaction vessel and/or one or more reagents, wherein said reagents comprise an ester of a polyhydric alcohol and a C1 to C18 carboxylic acid, a source of alkalinity and an oxidizing agent; wherein said feed pumps are in fluid connection with said reaction vessel and supply one or more reagents to produce said peroxycarboxylic acid forming composition in said reaction vessel; and wherein said reaction vessel is in fluid connection with said outlet to dispense said peroxycarboxylic acid forming composition.

In a still further embodiment, the present invention is a method of cleaning using an on-site generated peroxycarboxylic acid forming composition comprising: obtaining a user- or system-inputted peroxycarboxylic acid forming composition on-site using the adjustable biocide formulator or generator system of claim 11; and applying said peroxycarboxylic acid forming composition in an amount sufficient to sanitize, bleach or disinfect a surface in need thereof, wherein said composition retains within about 10% of its final concentration of peracid for at least about 1 minute, at least about 2 minutes, at least about 3 minutes, at least about 4 minutes, at least about 5 minutes, preferably within at least about 5-10 minutes, and more preferably for more than at least 10 minutes.

According to a preferred embodiment of the invention, the source of alkalinity is sodium hydroxide (e.g. caustic soda), and the sodium hydroxide is provided to said reaction vessel prior to the addition of said ester in a solution that is less than about 20 wt-% sodium hydroxide on an actives basis. Still further, the reaction goes to completion within less than about 30 minutes and the composition maintains a peracid concentration within about 10% of its final completion concentration for at least about 1 minute.

According to various preferred embodiments of the invention, the temperature control mechanism is selected from the group consisting of external heating or cooling of the reaction vessel, internal heating of the reagents within the reaction vessel, preheating one or more of the reagents, and combinations of the same. The embodiments of the invention may utilize a reaction vessel is a flow through reactor (e.g. continuous generation) or a batch reactor and the heated reagent is water. Still further, the composition may be neutralization with an acid or aqueous acidic solution when the concentration of peracid is within about 10% of its final concentration. More preferably, the composition is dispensed for use in a cleaning process when the concentration of peracid is within about 10% of its final concentration.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
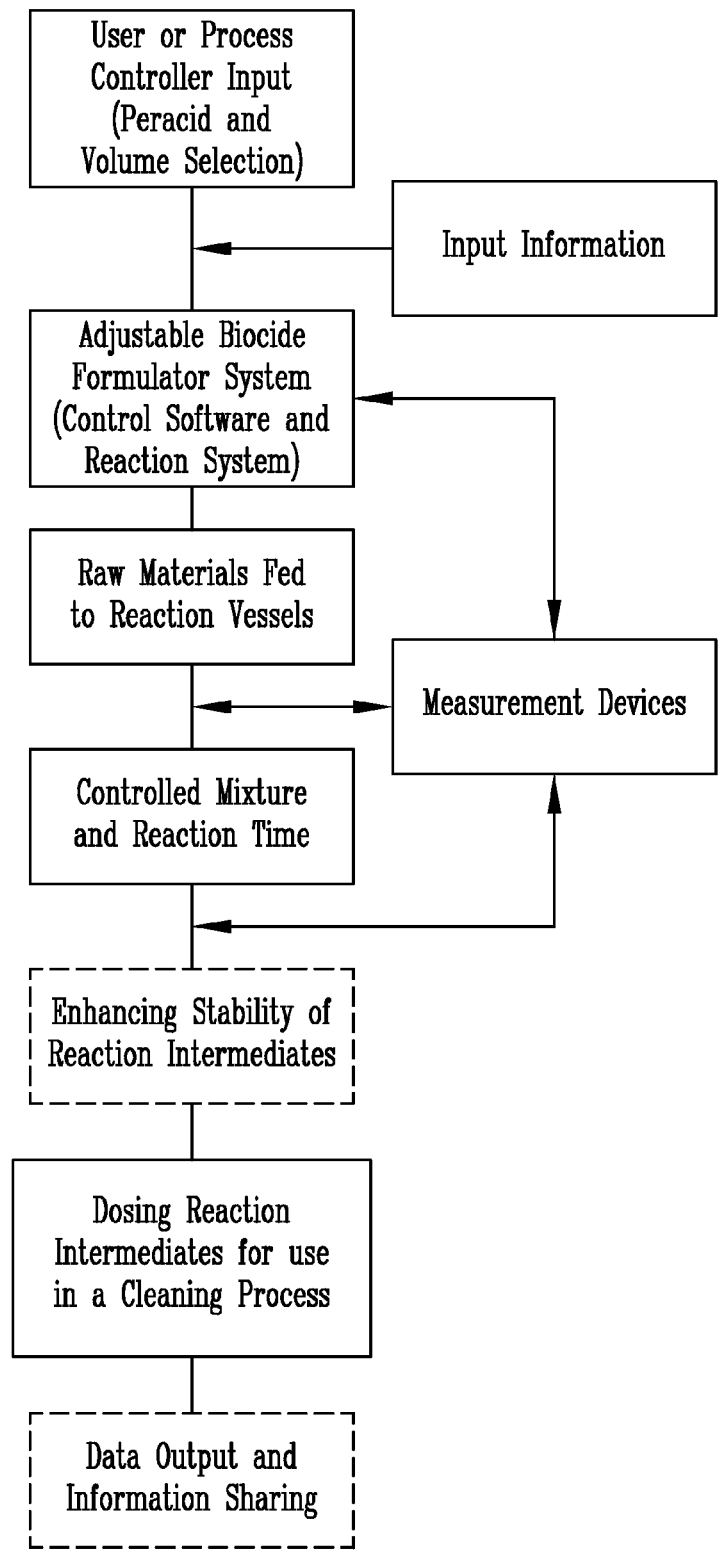
FIG. 1 shows a schematic diagram of a user or controller operated continuous adjustable biocide formulator apparatus according to the invention.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE INVENTION

The present disclosure relates to adjustable biocide formulator or generator systems for on-site peracid generation, including for example peroxycarboxylic acid forming compositions or peroxycarboxylic acids, as well as methods of making and using such compositions. The compositions and systems for making the compositions disclosed herein have significant advantages over conventional systems and methods for making peroxycarboxylic acids or peroxycarboxylic acid forming compositions. For example, the systems allow on-site, user- or system-controlled formulation, eliminating the step of shipping hazardous peroxycarboxylic acid compositions to an end user. In addition, there are various advantages of the compositions, including having significantly lower levels of reactants, increased stability and ability to be generated in situ.

The embodiments of this invention are not limited to particular methods and systems for on-site generation of sugar ester peracids for use as biocides, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers defining the range and include each integer within the defined range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

As used herein, "agricultural" or "veterinary" objects or surfaces include animal feeds, animal watering stations and enclosures, animal quarters, animal veterinarian clinics (e.g. surgical or treatment areas), animal surgical areas, and the like.

As used herein, the phrase "air streams" includes food anti-spoilage air circulation systems. Air streams also include air streams typically encountered in hospital, surgical, infirmity, birthing, mortuary, and clinical diagnosis rooms.

The term "cleaning," as used herein, means to perform or aid in soil removal, bleaching, microbial population reduction, or combination thereof As used herein, the term "disinfectant" refers to an agent that kills all vegetative cells including most recognized pathogenic microorganisms, using the procedure described in A.O.A.C. Use Dilution Methods, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, auto dish sanitizers, sanitizing gels, cooling towers, food processing antimicrobial garment sprays, and non-to-low-aqueous food preparation lubricants, oils, and rinse additives.

As used herein, the phrase "food product" includes any food substance that might require treatment with an antimicrobial agent or composition and that is edible with or without further preparation. Food products include meat (e.g., red meat and pork), seafood, poultry, produce (e.g., fruits and vegetables), eggs, living eggs, egg products, ready to eat food, wheat, seeds, roots, tubers, leafs, stems, corns, flowers, sprouts, seasonings, or a combination thereof. The term "produce" refers to food products such as fruits and vegetables and plants or plant-derived materials that are typically sold uncooked and, often, unpackaged, and that can sometimes be eaten raw.

As used herein, the term "fouling" shall be understood to mean the undesirable presence of or any deposition of any organic or inorganic material in the applicable composition or chemistry.

As used herein, the term "free" or "substantially free" refers to a composition, mixture, or ingredient that does not contain a particular compound or to which a particular compound or a particular compound-containing compound has not been added. Should the particular compound be present through contamination and/or use in a minimal amount of a composition, mixture, or ingredients, the amount of the compound shall be less than about 3 wt-%. More preferably, the amount of the compound is less than 2 wt-%, less than 1 wt-%, and most preferably the amount of the compound is less than 0.5 wt-%.

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.), or fabric surfaces, e.g., knit, woven, and non-woven surfaces (such as surgical garments, draperies, bed linens, bandages, etc.), or patient-care equipment (such as respirators, diagnostic equipment, shunts, body scopes, wheel chairs, beds, etc.), or surgical and diagnostic equipment. Health care surfaces include articles and surfaces employed in animal health care.

As used herein, the term "instrument" refers to the various medical or dental instruments or devices that can benefit from cleaning with a composition according to the present invention. As used herein, the phrases "medical instrument," "dental instrument," "medical device," "dental device," "medical equipment," or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, scopes (e.g., endoscopes, stethoscopes, and arthoscopes) and related equipment, and the like, or combinations thereof.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the terms "mixed" or "mixture" when used relating to "peroxycarboxylic acid composition" or "peroxycarboxylic acids" refer to a composition or mixture including more than one peroxycarboxylic acid, such as a composition or mixture including peroxyacetic acid (POAA) and peroxyoctanoic acid (POOA).

As used herein, the terms "mixed," "mixture" or "more than one" when used relating to esters suitable for use in forming the compositions of the invention refer to a composition or mixture including more than one ester group undergoing a perhydrolysis reaction to form the peroxycarboxylic composition. The use of at least one ester of a polyhydric alcohol and a C1 to C18 carboxylic acid according to the invention includes the use of various forms of the ester, such as the mono, di, tri and/or mixtures thereof formations of the particular ester. Accordingly, examples of suitable forms of esters for use as "mixtures" or comprising "more than one" include, but are not limited to, glycerol monooctanoate, glycerol dioctanoate, glycerol trioctanoate, sorbitan monooctanoate, sorbitan dioctanoate, sorbitan trioctanoate, and mixtures and derivatives thereof. Further, as one skilled in the art shall ascertain based upon the description of the invention disclosed herein, the use of an ester source, such as glycerol octanoate, may further comprise the use of the mono, di and tri esters and/or mixtures thereof. According to various embodiments of the invention, the use of "an" ester, such as octanoic glyceride, may include the use of a "mixture" of esters wherein more than one formation of the ester is present, including for example the mono, di and tri formations and/or mixtures thereof.

As used herein, the phrases "objectionable odor," "offensive odor," or "malodor," refer to a sharp, pungent, or acrid odor or atmospheric environment from which a typical person withdraws if they are able to. Hedonic tone provides a measure of the degree to which an odor is pleasant or unpleasant. An "objectionable odor," "offensive odor," or "malodor" has an hedonic tone rating it as unpleasant as or more unpleasant than a solution of 5 wt-% acetic acid, propionic acid, butyric acid, or mixtures thereof As used herein, the terms "peracid" or "peroxy acid" refer to an acid having the hydrogen of the hydroxyl group replaced by a hydroxy group. Oxidizing peracids are referred to herein as peroxycarboxylic acids.

As used herein, the term "polyhydric alcohol" or "polyol," refers to an alcohol that has two or more hydroxyl groups. Polyhydric alcohols suitable for use in the compositions include, but are not limited to, sugars, sugar alcohols, and mixtures and derivatives thereof.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25+/−2° C., against several test organisms.

As used herein the term "sugar" refers to carbohydrates including one, two, or more saccharose groups. Sugars are a group of organic compounds related by molecular structure that comprise simpler members of the general class of carbohydrates. Each sugar consists of a chain of 2 to 7 carbon atoms (usually 5 or 6). Sugars have the general formula $C_nH_{2n}O_n$, wherein n is between 2 and 7. One of the carbons carries aldehydic or ketonic oxygen which may be combined in acetal or ketal forms and the remaining carbon atoms usually bear hydrogen atoms and hydroxyl groups. In general, sugars are more or less sweet, water soluble, colorless, odorless, optically active substances which lose water, caramelize and char when heated. Exemplary sugars include, but are not limited to, glucose, sucrose, lactose and mixtures thereof.

As used herein, the term "sugar alcohol" refers to the hydrogenated form of a carbohydrate, wherein the carbonyl group of the carbohydrate has been reduced to a primary or secondary hydroxyl group. Sugar alcohols have the general formula $CH_2OH(CHOH)_nCH_2OH$, wherein n is from 2 to 5. Exemplary sugar alcohols include, but are not limited to, glycol, ethylene glycol, propylene glycol, glycerol, erythritol, pentaerythritol, threitol, arabitol, xylitol, ribitol, mannitol, sorbitol, sorbitan, dulcitol, iditol, inositol, isomalt, maltitol, lactitol, polyglycitol, 1,4-cyclohexane diol, and mixtures and derivatives thereof. In some embodiments, the sugar alcohol is selected from ethylene glycol, propylene glycol, glycerol, polyglycerol, sorbitol, sorbitan, and mixtures and derivatives thereof.

For the purpose of this patent application, successful microbial reduction is achieved when the microbial populations are reduced by at least about 50%, or by significantly more than is achieved by a wash with water. Larger reductions in microbial population provide greater levels of protection.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition.

As used herein, the term "ware" refers to items such as eating and cooking utensils, dishes, and other hard surfaces such as showers, sinks, toilets, bathtubs, countertops, windows, mirrors, transportation vehicles, and floors. As used herein, the term "ware washing" refers to washing, cleaning, or rinsing ware. Ware also refers to items made of plastic. Types of plastics that can be cleaned with the compositions according to the invention include but are not limited to, those that include polycarbonate polymers (PC), acrylonitrile-butadiene-styrene polymers (ABS), and polysulfone polymers (PS). Another exemplary plastic that can be cleaned using the compounds and compositions of the invention include polyethylene terephthalate (PET).

As used herein, the term "waters" includes food process or transport waters. Food process or transport waters include produce transport waters (e.g., as found in flumes, pipe transports, cutters, slicers, blanchers, retort systems, washers, and the like), belt sprays for food transport lines, boot and handwash dip-pans, third-sink rinse waters, and the like. Waters also include domestic and recreational waters such as pools, spas, recreational flumes and water slides, fountains, and the like.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

Embodiments of the Invention

Related Applications herein, the production of peracids ex-situ using an onsite mixing system is a complex process. In particular, related applications U.S. patent application Ser. No. 13/330,915 and U.S. Pat. No. 8,858,895, incorporated herein by reference in its entirety, disclose various embodiments of both batch and continuous generators for on-site generation of peracid chemistry. These applications demonstrate the variety of factors impacting the rate at which an ester precursor is converted to a resultant peracid. This application provides methods for overcoming a significant limitation of using any adjustable biocide formulator or generator system disclosed therein—namely, temperature adjustments for the efficient and cost-effective use of any adjustable biocide formulator or generator system.

Temperature is a critical factor on the kinetics of both peracid production as well as the kinetics of peracid decomposition inside any adjustable biocide formulator or generator system. In particular, temperature becomes important when considering the variable environments in which an ex-situ peracid adjustable biocide formulator or generator system may be used. Often environments suitable for employing an adjustable biocide formulator or generator system might range in temperature from the very cold (e.g. about 34° F. (1° C.)) to the very hot (e.g. about 122° F. (50° C.)). Exemplary on-site locations for generation of the peracid chemistry according to the invention may include, for example, a cold or refrigerated dairy room. Alternatively, a warm ambient temperature would be expected from a process floor of a manufacturing plant where myriad of heat-generating machines are located. As a result, when an adjustable biocide formulator or generator system and the particular raw starting materials (e.g. reagents) are used under these variable conditions they produce unique peracid production and degradation curves which impact the ability to consistently deliver a required dose of chemistry. Establishing methods for eliminating these varying production and/or degradation curves overcomes a significant limitation and results in the consistent generation of peracid chemistries regardless of ambient temperature conditions.

According to an embodiment of the invention, the methods of the invention solve the problem caused by having variable reaction temperatures, which can negatively impact the output and stability of an ex-situ peracid reaction. According to the invention, the ABF systems and methods of use are insensitive to environmental (e.g. ambient) temperatures of the location of the apparatus and/or reagents used for the generation of peracid chemistry.

In particular, in one aspect the invention temperature controls are provided for the reaction vessel and/or reaction manifold to overcome (i.e. control) any variability in both environmental factors and heat generated during the progression of the reaction. In another aspect of the invention, temperature controls are provided to at least one raw starting material (e.g. reagent) that is input into an adjustable biocide formulator or generator system. According to additional embodiments a combination of temperature controls may be provided.

Temperature Controls of Reaction Vessels and/or Manifolds

The methods according to the invention may comprise, consist of and/or consist essentially of at least one temperature control for controlling the temperature of a portion of the adjustable biocide formulator or generator system. In one aspect of the invention the temperature controls comprise, consist of and/or consist essentially of adjusting or controlling the temperature of the reaction vessel and/or reaction manifold. In another aspect of the invention the temperature controls comprise, consist of and/or consist essentially of adjusting or controlling the temperature of at least one zone of the ABF system. Adjusting or controlling the temperature of a particular zone of the ABF system, such as the reaction vessel and/or reaction manifold, eliminates variability in temperature caused as a result of environmental factors.

According to an embodiment the temperature of raw starting materials added to an adjustable biocide formulator or generator system may vary as a result of ambient temperatures. In addition, according to an embodiment the temperature of the adjustable biocide formulator or generator system itself may vary as a result of ambient temperatures. As a result, temperature controls of at least one zone of the system can adjust for changes in ambient temperature and/or adjust the temperature for the peracid reaction to overcome such ambient temperatures. Preferably, the temperature zone adjusts the temperature of the reaction vessel (or the reaction manifold for a continuous system).

In addition, adjusting or controlling the temperature of the reaction vessel and/or reaction manifold eliminates variability in temperature caused by heat generated during the progression of the reaction (e.g. exothermic reaction of forming peracid chemistry). As one skilled in the art will ascertain based on the disclosure of the present invention, the temperature variation can vary significantly based on reaction conditions largely driven by heat of solution caused by dilution of the source of alkalinity (e.g. NaOH (50%)), reaction of that source of alkalinity with hydrogen peroxide and/or neutralization of acidity in the composition. The amount of heat generated through the exothermic reaction is dependent on a number of factors including for example, scale of the reaction and heat transfer properties of the reaction vessel. An exemplary range of temperature variations observed according to the embodiments swings we deal with are typically in the 10-50° f range.

According to an embodiment the control of the reaction vessel and/or reaction manifold temperature may require refrigeration and/or heating. In particular, in one aspect of the temperature control, the temperature is kept cool enough that the chemistry has a reasonable stability window once the peracid has been formed to be dispensed (e.g. maintains within +/−10% of its max for at least about 1-10 minutes). The cooling temperature control may be required to decrease the temperature as a result of the exothermic reactions that may degrade the peracid compositions of the invention. In addition, there are various safety considerations for a system to avoid increases in temperature, for example system temperatures in excess of 100° C. In an additional aspect of the temperature control, the temperature is kept warm enough that the reaction can reach the +/−10% max concentration in a reasonable period of time (e.g. 1-5 minutes or 3-10 minutes).

The means for achieving the temperature control according to these embodiments of the invention may include in one aspect the use of a constant temperature range of the apparatus. According to this embodiment the particular zone of the system to be temperature controlled (e.g. reaction vessel and/or reaction manifold) is put into the constant temperature zone housing a heat source. According to an embodiment of the invention, a continuous or flow through reactor embodied in a reaction manifold is more amenable to temperature control through the use of heat exchangers than the batch-mode ABF systems. This is a result of the temperatures within specific zones of the reaction manifold more easily controlled to achieve complex chemistries that are more difficult to achieve when using a batch-mode ABF system.

Suitable mechanisms for a temperature control mechanism for use in the systems and methods of the invention include, for example, external heating or cooling of a zone (e.g. reaction vessel) and/or the internal heating of the reagents from within the reaction vessel. The temperature control means for increasing the temperature may further include a warm water bath and/or a heating chamber. In an additional aspect of the invention, a temperature control means for increasing the temperature of the ABF system includes the flushing of the system with a hot water source. For example, a water source having a temperature of at least about 37° C. (100° F.), preferably at least about 48° C. (120° F.) is flushed through the system periodically (e.g. between batches) to increase the temperature of the system.

Additional exemplary mechanisms for increasing the temperature of the ABF system include the use of heat jacketing of the reaction vessel or a jacketed manifold within the system, which may be achieved through the use of a heated water jacket, for example. In addition, further exemplary mechanisms for increasing the temperature of the ABF system include the use of electro-heating films, heating mantles, heat exchangers and the like. One skilled in the art will ascertain additional means for affording increases in temperature of at least a portion of the adjustable biocide formulator or generator system.

In another aspect of the invention, means for achieving the temperature control wherein a decrease in temperature is required may include a cooling system in or around the particular zone of the system to be temperature controlled (e.g. reaction vessel and/or reaction manifold). For example, it may be desirable to have reaction vessels and/or reaction manifold under refrigeration. Additional mechanisms that may be suitable for use to cool a reaction vessel, reaction manifold and/or other components of the system may include, for example, a quenching mode, increased surface area, cooling jacket, venting systems, cold finger, and the like.

Temperature Controls of Reagents

The methods according to the invention may comprise, consist of and/or consist essentially of at least one means of tempering a reagent used according to the invention. For example, in one aspect a tempered reagent (e.g. water) may be input into a system according to the invention to control the temperature of the adjustable biocide formulator or generator system and/or the generated chemistry.

Suitable mechanisms for tempering a reagent include the preheating of the reagent. For example, a stock solution of a reagent may be housed within a water bath (e.g. warming/cooling) to modify the temperature of the reagent above or below the ambient temperature, as applicable. Thereafter, the temperature adjusted reagent is provided to the ABF system in a preheated manner suitable for use according to the methods of the invention.

Additional exemplary mechanisms for the tempering of a reagent include the use of electric blankets, hot or cold rooms, submersible heaters and the like. One skilled in the art will ascertain additional methods for adjusting the temperature of a reagent according to the invention.

Preferably, a reagent is heated (or cooled to temperature adjust as applicable) to approximately between about 21° C. to about 60° C. (70-140° F.), preferably between about 26° C. to about 54° C. (80-130° F.), and more preferably between about 32° C. to about 48° C. (90-120° F.).

ABF Systems for Making on-Site Peracid Compositions

All embodiments of the ABF systems disclosed in related applications U.S. patent application Ser. No. 13/330,915 and U.S. Pat. No. 8,858,895, herein incorporated by reference in its entirety, are suitable systems for application of the temperature controlled modifications disclosed herein according to the invention. The various descriptions, including claims, specification and figures, outlining ABF system for the on-site generation of peracid chemistries are incorporated by reference herein.

According to an aspect of the invention, as used herein, the terms ABF, ABF system/apparatus/generator and the like refer equally to the various embodiments of the invention disclosing the batch and continuous ABF apparatus and/or system. The ABF system produces peroxycarboxylic acid forming compositions, referring to the generation of peroxycarboxylic acids in situ, in a non-equilibrium reaction. In particular embodiments of the invention, the ABF generator system produces the anion capable of forming peroxycarboxylic acid upon acidification. According to additional aspects of the invention, the ABF system may produce peroxycarboxylic acids.

Beneficially, the ABF systems according to the invention provide for apparatuses designed to produce peracid chemistry in either a continuous manner or in batch preparations. These variations of the embodiments of the invention are capable of supplying chemistries in large and/or small quantities and production rates. Regardless of the generation mode and/or mechanism the ABF systems according to the invention generate peracid chemistry that goes to completion within less than about 30 minutes. In addition, without regard to the generation mode and/or mechanism the ABF systems according to the invention, the peroxycarboxylic acid forming composition and/or peracid composition maintains a peracid concentration within about 10% of its final completion concentration for at least about 1 minute, at least about 2 minutes, at least about 3 minutes, at least about 4 minutes, at least about 5 minutes, preferably within at least about 5-10 minutes, and more preferably for more than at least 10 minutes.

According to an embodiment, the peracid concentration achieved is between about 0.25 wt-% to about 20 wt-%. Preferably, the peracid concentration is at least about 4 wt-%, more preferably at least about 5 wt-%, and still more preferably at least about 6wt-% or at least about 7 wt-%. According to a preferred embodiment of the invention, the methods and systems of the present invention achieve particular peracid concentrations of peroxyacetic acid of at least about 6 wt-% and peroxyoctanoic acid of at least about 7 wt-%.

In some aspects, the system for on-site generation of peroxycarboxylic acid forming compositions may comprise, consist of and/or consist essentially of an apparatus for on-site peroxycarboxylic acid forming composition generation that is insensitive to environmental temperatures of the location of the apparatus and/or reagents comprising a reaction vessel, a series of feed pumps, an outlet for dosing a peroxycarboxylic acid forming composition from said reaction vessel and a controller for a user- or system-inputted selection device. The apparatus of the invention is further defined by the embodiments of feed pumps in fluid connection with the reaction vessel and supply the reagents to produce said peroxycarboxylic acid forming composition in the reaction vessel. Further embodiments include the reaction vessel in fluid connection with said outlet to dispense the peroxycarboxylic acid forming composition. According to the beneficial embodiments of the invention, the temperature controlled mechanism maintains a controlled temperature of the reaction vessel and/or one or more reagents.

In additional preferred embodiments of the system, the mix order of reagents are controlled to produce a consistent output of peracid chemistry without any fouling (e.g. precipitation or phase separation) of the reagents. In further aspects, the system employs an alkalinity source that is sodium hydroxide (e.g. caustic soda). Further, the sodium hydroxide is provided to the reaction vessel prior to the addition of the ester in a solution that is less than about 20 wt-% sodium hydroxide on an actives basis. In one aspect of the invention, the source of alkalinity (e.g. sodium hydroxide or caustic soda) is combined with water (e.g. diluted) prior to the addition of the ester source. As disclosed herein the ester source can further be provided in an ester premix (e.g. ester/peroxide premix).

In additional preferred embodiment of the invention, the concentration of the source of alkalinity are controlled to produce a consistent output of peracid chemistry without any fouling (e.g. precipitation) of the reagents. In particular a NaOH solution that is no more than 20 wt-% on an actives basis is obtained by diluting the NaOH with a water source before the ester component is combined with the reagents. Although not intending to be limited according to any theory of the invention and/or mechanism of action, the invention demonstrates superior peracid generation when a system delivers a source of alkalinity (e.g. NaOH solution) source that is no more than 20% on an actives basis before combining with the ester reagent to initiate the peracid production reaction.

According to preferred embodiments of making the peracid chemistry, an ex-situ ABF generator system using an injection manifold to combine an alkaline source, an ester precursor, a peroxygen source and optionally water for production of a peroxy acid is used. Preferably the alkaline source is caustic soda, wherein the caustic stream feeding the manifold is less than about 20% by weight. In an aspect the caustic can be diluted within the manifold to the target concentration of less than about 20% by weight. In an additional embodiment, the ester is added to the system downstream (e.g. after the addition of the diluted NaOH solution).

The systems may further comprise, consist of and/or consist essentially of at least one measurement device, wherein said measurement device measures one or more reaction kinetics or system operations for said peroxycarboxylic acid forming composition generation selected from the group consisting of fluorescence, weight, flow, capacitive level, pH, oxidation reduction potential, pressure, temperature and combinations thereof Such measurement devices are those suitable to measure one or more reaction kinetics or system operations for the generation of peroxycarboxylic acid forming compositions, including for example devices to measure fluorescence, weight, flow (e.g. flow meters or switches), capacitive level, pH, oxidation reduction potential, pressure, temperature and combinations thereof. Such measurement devices may measure the system's feed pumps, reaction vessels, reservoir, outlets, etc. Examples of additional suitable measurement devices include capacitive level sensors, out of product alarms, POA/peroxide monitors, oxychecks, IR/UV/VIS spectroscopy and pressure switches. Still further examples of suitable measurement devices are disclosed herein, in addition various embodiments of those disclosed in U.S. patent application Ser. No. 12/108,202, and U.S. Pat. No. 7,547,421, both entitled Apparatus and Method for Making Peroxycarboxylic Acid, which are herein incorporated by reference in their entirety.

According to a further embodiment, the systems may comprise, consist of and/or consist essentially of an additional feed pump providing an acid or acidic aqueous solution in fluid communication with the reaction manifold or said reservoir. This feed pump is used to provide the acid or acidic aqueous solution to dilute the peroxycarboxylic acid forming composition to form a peroxycarboxylic acid having a pH of about 1.0 to about 8.0. According to an embodiment the neutralization with the acid or aqueous acidic solution takes place when the concentration of peracid is within about 10% of its final concentration.

According to further embodiments, the systems may comprise, consist of and/or consist essentially of an sources of additional reagents as disclosed according to the compositions of the invention herein. One skilled in the art will ascertain the non-limiting examples of the systems herein are further understood to include the various embodiments of the invention disclosed with regard to the compositions and methods of making the same according to the invention (e.g. use of additional/alternative reagents, reagent formulations, input means, order of mixing/adding reagents, and the like).

In some aspects of the invention, the system may include a variety of safety mechanisms. Exemplary on-site safety feedback mechanisms for a system are disclosed in further detail in U.S. Patent Publication No. 2009/0208365, which is hereby expressly incorporated by reference including, without limitation, the specification, claims, and abstract, as well as any figures, tables, or drawings thereof. Various safety mechanisms can measure pressure, temperature, difference in pressure, difference in temperature, or a combination thereof and provide a perceptible signal if one or more of these increases above a predetermined level. The level of pressure, temperature, difference in pressure, difference in temperature, or a combination thereof at which safety system provides a perceptible signal can be selected to allow intervention to avoid undesirable or unsafe conditions.

In some aspects, the system for making on-site peracid chemistry formulations further comprises an optional controller or software platform. The software platform provides a user or system to select a generation mode for a desired peracid formulation for on-site generation. As a result, use of the system for onsite peracid chemistry generation provides significant user flexibility to generate chemistries for particular user-identified purposes. For example, the controller or control software for operation of the system may permit a user or system to select both the peracid formulation and the desired volume of the formulation for on-site generation. In a further aspect, the control software may determine the timing, sequencing and/or selection of feeding raw materials (e.g. reagents) into the system, mixing time and total reaction time required for production of the user- or system-selected peracid formulation.

According to the invention, the controller may further include a mechanism for manually starting/stopping any of the same functions, including for example a manual switch panel for the same. In addition to manual controls, such as a manual switch panel, the controller preferably has buttons or other means for selecting particular embodiments according to option displayed by the control software platform. An embodiment of the controller may further include a display screen to assist a user in selecting a generation mode for a desired peracid formulation and any other options for user selection as one skilled in the art will ascertain based upon the description of the invention. Concomitant with the control software are user-friendly instructions for use displayed on the display screen (or the like).

In an aspect of the invention, the control software utilizes a control software algorithm to maximize on-site active chemistry yield and provide safe operating conditions for the reactor vessel(s) of the system. The control software permits user-identified chemistry production to be run in one or multiple reaction vessels and to properly sequence reactions to obtain active chemistries.

Examples of suitable controllers are disclosed herein, in addition various embodiments of those disclosed in U.S. patent application Ser. No. 12/108,202, and U.S. Pat. No. 7,547,421, both entitled Apparatus and Method for Making Peroxycarboxylic Acid, which are herein incorporated by reference in their entirety.

In another aspect of the invention, the system may include a data output means for sharing information related to the peroxycarboxylic acid forming compositions and/or peroxycarboxylic acid formulations generated according to the system. For example, an information backbone may be used to both collect and disseminate data from the process of generating the peracid formulations including, for example, composition consumption, dispensing or usage, and additional formulation production-related data. Such data may be generated in real-time and/or provided in a historical log of operational data detectable or storable by a user or system. In an embodiment of the invention a user or system is able to monitor usage and performance, including for example, chemistry dispensing, managing chemistry distribution to various point-of-use applications, communication with system operators to control and monitor chemistry dispensing, allocation and/or formulation and the like. According to an additional embodiment of the invention, a user or system is able to control systems, including program systems, remotely.

According to an aspect of the invention, any system operations suitable for use with the invention may be controlled and/or monitored from a remote location. Remote system operations control and/or monitoring may further include the system updates and/or upgrades. According to an aspect of the invention updates and/or upgrades to system operations may be downloaded remotely. These and other embodiments of data output means, information sharing, remote system operations and the like, which may be adapted for use with the present invention, are further described, for example, in U.S. Pat. Nos. 7,292,917, 6,895,307, 6,697,706 and 6,377,868 and U.S. Patent Publication Nos. 2005/0102059, 2005/0065644, 2004/0088076, 2003/0195657 and 2003/0195656, which are hereby expressly incorporated by reference including, without limitation, the specification, claims, and abstract, as well as any figures, tables, or drawings thereof.

In another aspect of the invention, the data output for sharing information related to the compositions according to the system may coordinate multiple systems on at a single site. According to this embodiment of the invention, information sharing between the multiple systems may take places place using any communications network capable of coupling one or more systems according to the present invention, including for example, using a server computer and a database.

Exemplary Systems Depicted by Figures

According to an embodiment of the invention, as shown in FIG. 1, a user or process controller input, such as a CIP or tunnel washer process controller, selects a peracid formulation desired for on-site generation for a specific cleaning application. The user or process controller input selects both the chemistry formulation and how much is needed (i.e., gallons use solution) and such input information is loaded into the ABF system. Control software, including a software algorithm, may be used to calculate the timing and sequencing for dosing the raw materials needed for the particular peracid chemistry generation. Raw materials are fed into the reaction vessels of the system under controlled mixture and reaction times. The system may employ a variety of measurement devices providing feedback to the system. Optionally, for generation of a peroxycarboxylic acid formulation (as opposed to the anion peroxycarboxylic acid forming compositions), the stability of the reaction intermediates may be enhanced by adding an acid or aqueous acidic solution. The system provides the user or process controller selected peracid formulation for use in a cleaning process, including without limitation, antimicrobial, bleaching, sanitizing and/or antiscaling applications. In addition, various data output and information sharing methods may optionally be employed according to the methods and systems of the invention.

Figure 2A:
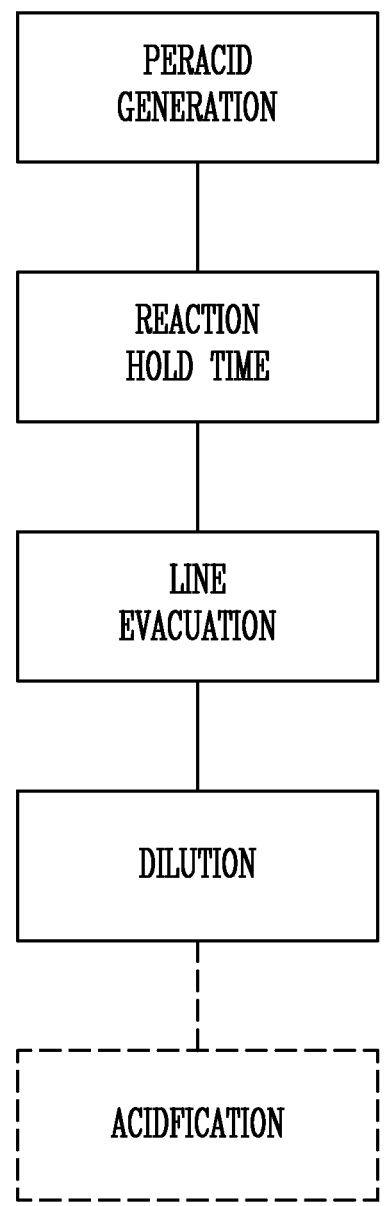
FIGS. 2A-B show diagrams of an embodiment of an adjustable biocide formulator apparatus according to the invention, including description of the dosing of raw starting materials (e.g. reagents) for the generation of peracid chemistries according to the invention.
Figure 2B:
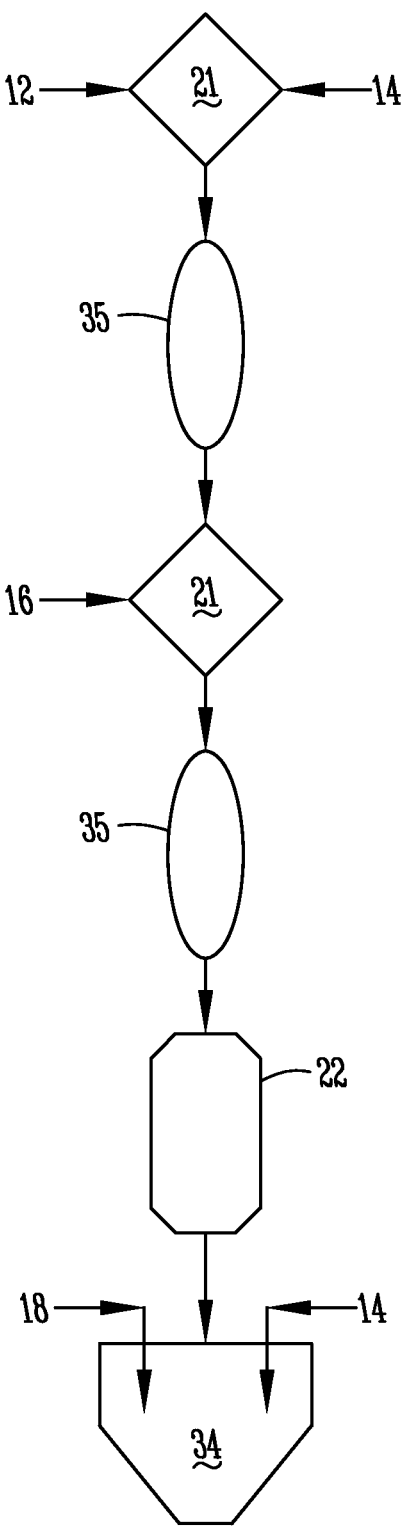

FIGS. 2A and 2B show diagrams of an embodiment of an adjustable biocide formulator apparatus according to the invention, including description of the dosing of raw starting materials (e.g. reagents) for the generation of peracid chemistries according to the invention. In particular, FIG. 2A shows a process flow of methods of making the peracid chemistry using the apparatus according to the invention. The methods set forth can be utilized using either a batch or a continuous generator according to the various embodiments of the invention. As set forth, methods of the invention include the steps of peracid generation, a period of reaction holding time followed by evacuation of the line, dilution with water of the concentrated chemistry and optionally acidification.

FIG. 2B further shows a non-limiting example of a method of peracid chemistry according to FIG. 2A. In the non-limiting example peracid generation includes the injection of raw starting materials (e.g. reagents). In particular, the injection of NaOH 12 and water 14 are combined in injection manifold 21. The injection manifold is not limited according to a particular structure or apparatus. According to a preferred embodiment, the caustic is diluted to a concentration of less than or equal to about 20% by weight. The NaOH 12 and water 14 are preferably homogenized or mixed by passing through a mixer 35. Thereafter, the an ester premix or ester and peroxide 16 are injected into another injection manifold 21 of the system. According to this aspect of the invention the ester premix or ester and peroxide are added to the dilute NaOH for improved chemistry generation. The ester premix or its individual components 16 are homogenized or mixed 35 with the caustic stream. Following the mixing, the reagents are held for the reaction to go to completion within a reaction manifold 22. Notably, the holding step can occur direction in a dilution tank 34 or optionally in an intermediate reaction manifold 22. Following the reaction hold time the reaction manifold 22 is purged with water then air into a dilution vessel 34 (e.g. line evacuation). Then water 14 is used for the dilution step within the dilution tank 34 to dilute the concentrated chemistry. In a further aspect the diluted chemistry can be acidified using an acid or aqueous acid solution 18 within the dilution vessel 34 (or optionally within the reaction manifold 22—not depicted in the figure). Upon completion of the peracid generation as depicted in FIGS. 2A-B a water source 14 may be used to flush the system at a high flow rate.

Apparatus Dosing

The apparatus of the ABF system overcomes the raw material feed design challenge of accurately dosing raw materials. According to the invention, liquid based raw materials must be dosed into reaction vessel(s) quickly. For example, according to an embodiment of the invention, the sugar ester is the limiting reaction ingredient and requires accurate dispensing of the raw material. An example of a suitable sugar ester is sorbital octanoate and/or glyceryl octanoate, which are viscous liquids that are difficult to accurately measure. As a result, pump selection is critical and accommodating pump characteristics with software is a critical embodiment of the ABF system.

The dispensing precision required to prepare small batch sizes is more critical than larger batches, as a result of the dispensing error becoming a larger percentage of the dispensed peracid chemistries. As a result, the apparatus of the ABF system provides feed pumps to reduce the presence of air bubbles in the delivery line altering the amount of sugar ester chemistry dispensed and reducing the overall yield of the reaction. In addition to providing suitable feed pumps, the concentration of the sugar ester may be diluted to increase dosing accuracy. Such methods improve the dosing accuracy and decrease variations in volumetric flow of reagents according to the invention. In addition to the reduction of air bubbles in a delivery line, the dispensing precision according to the invention delivers the reagents at a constant flow rate over long durations of time, thereby reducing and/or eliminating the need for recalibration of the apparatus.

According to an alternative embodiment of the invention, a viscosity modifier may be added to the sugar ester. A viscosity modifier is a further example of a suitable raw material 28 according to the invention. Viscosity modifiers according to the invention may be used to adjust the rheology of a reagent in order to reduce the viscosity to make a raw material more suitable for use in the apparatus and system according to the invention, namely rendering the raw material significantly easier to pump.

Apparatus Rinsing

Rinsing of the ABF system has an impact on yield. According to an embodiment of the invention, adequate rinsing of the reactor vessel(s) and feed pump lines is necessary.

According to a preferred embodiment of the invention, the control software of the ABF system may be used to establish a process for system rinsing both reactor vessel(s) and feed pump lines. Remaining water after rinsing or flushing does not have a negative impact on the system. Water remaining in the mixing manifold imparts a dilution factor for which the dilution factor can be accommodated in the formulation. However, reaction intermediates must be rinsed from the system, as any reacted chemistry not flushed impacts the yield of a subsequent batch. This is a result of residual reaction intermediates in the system imparting unknown actives concentration due to the instability of the product at high pH over time. In addition, according to an embodiment an air-purge may be further employed after rinsing of the apparatus according to the invention, which as one skilled in the art will appreciate effectively removes nearly all liquid content from the manifold after a water rinse.

Preferably, the ABF system, including the reaction vessels, is cleaned between batches of peroxycarboxylic acid forming compositions. According to an embodiment of the invention, the system is rinsed (e.g. feed pump lines flushed) with warm/hot water between batches, and/or at regularly schedules intervals to comply with regulatory requirements (e.g. sanitizing regulations), as one skilled in the art shall ascertain. According to embodiments employing a continuous system the feed pump lines (including reaction manifold) may be rinsed at scheduled increments.

Compositions

The embodiments of the invention are suitable for generating the peroxycarboxylic acid chemistries (as well as the anion peroxycarboxylic acid forming compositions) which are disclosed in further detail in the related U.S. patent application Ser. Nos. 61/427,965, 13/331,304, now issued U.S. Pat. No. 8,846,107, and Ser. No. 13/331,486, entitled In Situ Generation of Peroxycarboxylic Acids at Alkaline pH and Methods of Use Thereof, which are herein incorporated by reference in its entirety. In addition to the chemistries generated, these applications incorporated by reference further disclose the particular raw starting materials (e.g. reagents) suitable for use in the ABF systems according to the invention to generate the particular chemistries.

In some embodiments, the system according to the present invention produces peroxycarboxylic acid forming compositions or peroxycarboxylic acid compositions for use in a variety of cleaning applications. The compositions have enhanced stability. According to an embodiment of the invention, the peroxycarboxylic acid forming compositions are stable for up to 24 hours providing suitable stability for on-site generation and usage for a variety of cleaning applications. According to a further embodiment, the peroxycarboxylic acid compositions are stable for up to at about 7 to 10 days.

In some aspects, the present disclosure relates to peroxycarboxylic acid forming compositions. That is, the compositions are capable of generating peroxycarboxylic acids in situ, in a non-equilibrium reaction. Surprisingly, it has been found that the optimum pH for the generation of peroxycarboxylic acid compositions is greater than about 12, or pH greater than about 13. It has also been found that mixed peroxycarboxylic acid compositions, viz. compositions that form two or more peroxycarboxylic acids, can be generated in situ in accordance with the methods disclosed herein. Peroxycarboxylic (or percarboxylic) acids generally have the formula $R(CO_3H)_n$, where, for example, R is an alkyl, aryl alkyl, cycloalkyl, aromatic, or heterocyclic group, and n is one, two, or three, and named by prefixing the parent acid with peroxy. The R group can be saturated or unsaturated as well as substituted or unsubstituted.

In an embodiment of the invention the peroxycarboxylic acid forming compositions comprise individual reagents combined according to the invention. These reagents are described herein individually along and include at least one ester of a polyhydric alcohol and a C1 to C18 carboxylic acid, an oxidizing agent, a source of alkalinity, solvents, and other functional groups. An acidulant is also described herein as a reagent to be added to the compositions after the formation of the percarboxylic acid(s). Alternatively, as described herein, there may be benefits to providing the reagents in various premix formulations to decrease the number of reagents and/or increase the simplicity of the invention. Each of these embodiments are described in further detail herein.

Esters

In some aspects, the compositions include an ester of a polyhydric alcohol and a C1 to C18 carboxylic acid. According to an embodiment, the polyhydric alcohol may also include a sugar alcohol. The compositions can also include more than one or a mixture of esters of a polyhydric alcohol and a C1 to C18 carboxylic acid. For example, in some embodiments, the compositions include two, three or four esters. When more than one ester is present, the esters can be different. For example, in some embodiments, the compositions can include a first ester of a polyhydric alcohol and a C1 to C4 carboxylic acid, and a second ester of a polyhydric alcohol and a C5 to C11 carboxylic acid. For further example, in some embodiments, the compositions can include a first ester of a polyhydric alcohol and a C1 to C18 carboxylic acid in a mono, di or tri-formation, and a second ester of a polyhydric alcohol and a C1 to C18 carboxylic acid in a mono, di or tri-formation. One skilled in the art will appreciate the various combinations of esters that can be used for the compositions according to the invention.

An example of a suitable ester for use according to the invention is glycerol octanoate. Glycerol octanoate has multiple ester components and others, including glycerol monooctanoate, glycerol dioctanoate, glycerol trioctanoate and others (glycerin, fatty acid, water). An estimated component percentage of each is approximated at about 39.6% glycerol monooctanoate, 24.5% glycerol dioctanoate, 1.42% glycerol trioctanoate and 34.5% of the others (glycerin, fatty acid, water).

The use of various forms of an ester (e.g. mono, di and/or tri-formations) to comprise a mixture of esters will impact the peracid yield of a particular composition according to the invention. For example, the various forms of the ester will have different kinetics in generating the peracids according to the methods of the invention. For example, in one aspect, a monooctanoate glycerol ester is faster in generating peracid than the di- or trioctanoate glycerol esters. In addition, the selection of the various forms of an ester will be further impacted by the water solubility of the compositions and whether any additional ingredients are combined to affect solubility (e.g. solvents) that would favor the use of less soluble ester forms (e.g. tri-formations). Accordingly, one skilled in the art of reaction kinetics will ascertain the benefits of using various combinations or mixtures of esters according to the compositions and methods of the invention.

The esters for use in the present invention include esters of polyhydric alcohols with carboxylic acid based leaving groups. A variety of carboxylic acids can be included. Carboxylic acids generally have the formula R(COOH)n, where, for example, R is an alkyl, aryl alkyl, cycloalkyl, aromatic, or heterocyclic group, and n is one, two, or three. In some embodiments, the carboxylic acid leaving group is a $C_5$ to $C_{11}$ carboxylic acid. In some embodiments, the carboxylic acid leaving group is a $C_1$ to $C_4$ carboxylic acid. In other embodiments, the compositions include two esters of polyhydric alcohols, each ester having a different carboxylic acid leaving group. For example, the compositions can include a polyhydric alcohol ester with a C1 to C4 carboxylic acid leaving group, and also include a polyhydric alcohol ester with a C5 to C11 carboxylic acid leaving group.

Examples of suitable carboxylic acids include, but are not limited to, formic, acetic, propionic, butanoic, pentanoic, hexanoic, heptanoic, octanoic, nonanoic, decanoic, undecanoic, dodecanoic, as well as their branched isomers, lactic, maleic, ascorbic, citric, hydroxyacetic, neopentanoic, neoheptanoic, neodecanoic, oxalic, malonic, succinic, glutaric, adipic, pimelic subric acid, and mixtures thereof.

Without wishing to be bound by any particular theory, it is thought that the esters included in the compositions undergo a perhydrolysis reaction, thereby forming the peroxycarboxylic composition. An exemplary perhydrolysis reaction in accordance with the present disclosure is illustrated below:

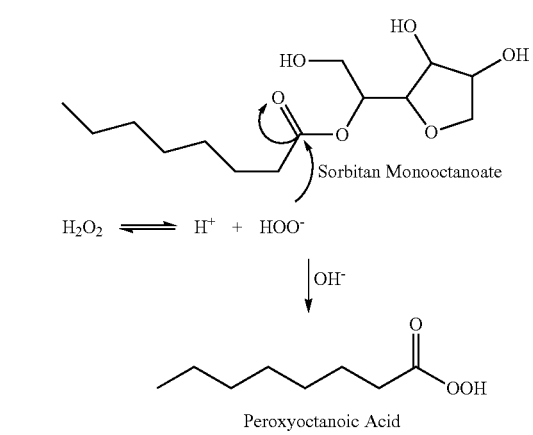

Peroxyoctanoic Acid

As can be seen from this illustration, it is thought the oxidizing agent, $H_2O_2$, perhydrolyzes the ester bond, thereby forming the percarboxylic acid corresponding to the cleaved carboxylic acid group. In contrast to an acid catalyzed equilibrium reaction, the reaction is stoichiometric, i.e. no excess amounts of the reactants are required for the reaction. The kinetics of the reaction are pH dependent, and the reaction can reach the maximum yield in the order of minutes. Esters suitable for use include, but are not limited to, monooctanoic glyceride, dioctanoic glyceride, trioctaonoic glyceride, polyglycerol octanoate, sorbitan monooctanoate, sorbitan dioctanoate, sorbitan trioctanoate, laurate sucroside and mixtures and derivatives thereof.

The compositions include the esters in an amount sufficient to generate the desired amount of percarboxylic acid. In some embodiments, the compositions include about 0.01 wt-% to about 95 wt-% of the ester, about 0.1 wt-% to about 50 wt-% of the ester, or about 1 wt-% to about 10 wt-% of the ester. In some embodiments, more than one ester is present in the compositions. Each ester can be present in the compositions at the above stated weight percents.

Unlike conventional acid catalyzed equilibrium peroxycarboxylic acid forming compositions, the compositions of the present invention can be formed using a non-equilibrium perhydrolysis reaction. Thus, an excess amount of the starting reagents is not needed. Accordingly, after formation of the peroxycarboxylic acid, the compositions contain less carboxylic acid and more peroxycarboxylic acid than an equivalent equilibrium reaction. In some embodiments, the compositions contain about 1 part percarboxylic acid for every about 1 part carboxylic acid after perhydrolysis, or about 6 part percarboxylic acid for every about 1 part carboxylic acid after perhydrolysis. In some embodiments, the compositions are free of or substantially free of carboxylic acids after the perhydrolysis reaction.

Alkalinity Source

The compositions also include a source of alkalinity. The source of alkalinity can include, but is not limited to, an alkaline metal hydroxide, an alkaline earth metal hydroxide, an alkali metal silicate, an alkali metal carbonate, borates and mixtures thereof. Suitable alkaline metal hydroxides include, but are not limited to, sodium hydroxide, potassium hydroxide and mixtures thereof. Suitable alkaline earth metal hydroxides include, but are not limited to, magnesium hydroxide, calcium hydroxide and mixtures and derivatives thereof. Suitable alkali metal silicates include but are not limited to, sodium silicate and derivatives thereof. In other embodiments, an alkali metal carbonate can be used as a source of alkalinity. For example, in some embodiments, sodium carbonate, sodium bicarbonate or mixtures and derivatives thereof can be used.

The source of alkalinity can be present in the compositions in an amount sufficient to provide the desired pH. In some embodiments, the compositions have a pH greater than about 12, greater than about 12.5, or greater than about 13. In some embodiments, the alkaline source is present in the composition from about 0.001 wt-% to about 50 wt-%, from about 1 wt-% to about 30wt-%, or about 10 wt-% to about 25 wt-%. In some embodiments, the alkaline source is present at from about 25 wt-% to about 50 wt-% of the composition. It is to be understood that all ranges and values between these ranges and values are encompassed by the present disclosure.

Oxidizing Agent

The compositions also include an oxidizing agent. The oxidizing agent may include a peroxide source. Oxidizing agents suitable for use with the compositions include the following types of compounds or sources of these compounds, or alkali metal salts including these types of compounds, or forming an adduct therewith: hydrogen peroxide, urea-hydrogen peroxide complexes or hydrogen peroxide donors of: group 1 (IA) oxidizing agents, for example lithium peroxide, sodium peroxide; group 2 (IIA) oxidizing agents, for example magnesium peroxide, calcium peroxide, strontium peroxide, barium peroxide; group 12 (IIB) oxidizing agents, for example zinc peroxide; group 13 (IIIA) oxidizing agents, for example boron compounds, such as perborates, for example sodium perborate hexahydrate of the formula $Na_2[B_2(O_2)_2(OH)_4]\cdot6H_2O$ (also called sodium perborate tetrahydrate); sodium peroxyborate tetrahydrate of the formula $Na_2B_2(O_2)_2[(OH)_4]\cdot4H_2O$ (also called sodium perborate trihydrate); sodium peroxyborate of the formula $Na_2[B_2(O_2)_2(OH)_4]$ (also called sodium perborate monohydrate); group 14 (IVA) oxidizing agents, for example persilicates and peroxycarbonates, which are also called percarbonates, such as persilicates or peroxycarbonates of alkali metals; group 15 (VA) oxidizing agents, for example peroxynitrous acid and its salts; peroxyphosphoric acids and their salts, for example, perphosphates; group 16 (VIA) oxidizing agents, for example peroxysulfuric acids and their salts, such as peroxymonosulfuric and peroxydisulfuric acids, and their salts, such as persulfates, for example, sodium persulfate; and group VIIa oxidizing agents such as sodium periodate, potassium perchlorate. Other active inorganic oxygen compounds can include transition metal peroxides; and other such peroxygen compounds, and mixtures thereof.

In some embodiments, the compositions of the present invention employ one or more of the inorganic oxidizing agents listed above. Suitable inorganic oxidizing agents include ozone, hydrogen peroxide, hydrogen peroxide adduct, group IIIA oxidizing agent, or hydrogen peroxide donors of group VIA oxidizing agent, group VA oxidizing agent, group VIIA oxidizing agent, or mixtures thereof. Suitable examples of such inorganic oxidizing agents include percarbonate, perborate, persulfate, perphosphate, persilicate, or mixtures thereof.

In some embodiments, the oxidizing agent includes hydrogen peroxide, or a source or donor of hydrogen peroxide. In other embodiments, the oxidizing agent includes a peroxide source selected from a percarbonate, a perborate urea hydrogen peroxide, PVP-peroxides and mixtures thereof.

The compositions may contain an effective amount of an oxidizing agent. In some embodiments, the compositions include about 0.001 wt-% to about 60 wt-% of the oxidizing agent, or about 1 wt-% to about 25 wt-% of the oxidizing agent. In some embodiments, the compositions include about 30 wt-% to about 50 wt-% of the oxidizing agent. It is to be understood that all ranges and values between these ranges and values are encompassed by the present invention.

Solvent

In some embodiments, the compositions of the invention further include a solvent. In some embodiments, the solvent is water. The water may be provided by the use of aqueous reagents, viz. oxidizing agent, alkalinity source. In other embodiments, an additional amount of water is added to the compositions. The compositions may be free of or substantially free of any added water. A non-aqueous solvent may also be used in the compositions. For example, in some embodiments, an alcohol is included as a solvent in the compositions.

The compositions may include an effective amount of solvent. In some embodiments, the compositions may include about 10 wt-% to about 99 wt-% of a solvent, or about 20 wt % to about 80 wt-% of a solvent. In other embodiments, the compositions may include more than about 30 wt-%, more than about 50 wt-%, more than about 60 wt-% or more than 70% of a solvent. It is to be understood that all values and ranges between these values and ranges are encompassed by the present invention.

Eliminated Functional Ingredients

Unlike conventional equilibrium based peroxycarboxylic acid compositions, the compositions disclosed herein are formed from a non-equilibrium reaction. Further, the composition disclosed herein can be used immediately after generation. Thus, many of the additional ingredients required in equilibrium based compositions do not need to be included in the present compositions. In some embodiments stabilizing agents are preferred for certain compositions according to the invention and provide benefits. However, beneficially, the use of non-equilibrium chemistry according to the present invention optionally provides that the compositions can be free of, or substantially free of a stabilizing agent.

Stabilizing agents are commonly added to equilibrium peroxycarboxylic acid compositions to stabilize the peracid and hydrogen peroxide and prevent the decomposition of these constituents within the compositions. Various embodiments of the invention do not require the use of at least one or more of such stabilizing agents. Examples of stabilizing agents may include for example, surfactants, couplers, hydrotropes, acid catalysts and the like that are conventionally used in equilibrium peracid compositions to stabilize and improve shelf life of the composition.

Further examples of stabilizing agents include, for example, chelating agents or sequestrants. Such sequestrants include, but are not limited to, organic chelating compounds that sequester metal ions in solution, particularly transition metal ions. Such sequestrants include organic amino- or hydroxy-polyphosphonic acid complexing agents (either in acid or soluble salt forms), carboxylic acids (e.g., polymeric polycarboxylate), hydroxycarboxylic acids, aminocarboxylic acids, or heterocyclic carboxylic acids, e.g., pyridine-2,6-dicarboxylic acid (dipicolinic acid). Dipicolinic acid, 1-hydroxy ethylidene-1,1-diphosphonic acid ($CH_3C(PO_3H_2)_2OH$) (HEDP) are further example of stabilizing agents.

Additional examples of stabilizing agents commonly used in equilibrium chemistry to stabilize the peracid and hydrogen peroxide and/or prevent the premature oxidation of the composition include phosphonic acid or phosphonate salt. Phosphonic acids and phosphonate salts include HEDP; ethylenediamine tetrakis methylenephosphonic acid (EDTMP); diethylenetriamine pentakis methylenephosphonic acid (DTPMP); cyclohexane-1,2-tetramethylene phosphonic acid; amino[tri(methylene phosphonic acid)]; (ethylene diamine[tetra methylene-phosphonic acid)]; 2-phosphene butane-1,2,4-tricarboxylic acid; or salts thereof, such as the alkali metal salts, ammonium salts, or alkyloyl amine salts, such as mono, di, or tetra-ethanolamine salts; picolinic, dipicolinic acid or mixtures thereof. In some embodiments, organic phosphonates, e.g., HEDP are well known as used stabilizing agents.

Exemplary commercially available food additive chelating agents include phosphonates sold under the trade name DEQUEST® including, for example, 1-hydroxyethylidene-1,1-diphosphonic acid, available from Monsanto Industrial Chemicals Co., St. Louis, Mo., as DEQUEST® 2010; amino (tri(methylenephosphonic acid)), (N[$CH_2PO_3H_2$]$_3$), available from Monsanto as DEQUEST® 2000; ethylenediamine [tetra(methylenephosphonic acid)] available from Monsanto as DEQUEST® 2041; and 2-phosphonobutane-1,2,4-tricarboxylic acid available from Mobay Chemical Corporation, Inorganic Chemicals Division, Pittsburgh, Pa., as Bayhibit AM. Further exemplary sequestrant can be or include aminocarboxylic acid type sequestrant. Suitable aminocarboxylic acid type sequestrants include the acids or alkali metal salts thereof, e.g., amino acetates and salts thereof. Suitable aminocarboxylates include N-hydroxyethylaminodiacetic acid; hydroxyethylenediaminetetraacetic acid, nitrilotriacetic acid (NTA); ethylenediaminetetraacetic acid (EDTA); N-hydroxyethyl-ethylenediaminetriacetic acid (HEDTA); diethylenetriaminepentaacetic acid (DTPA); and alanine-N, N-diacetic acid; and the like; and mixtures thereof. Still further sequestrants include polycarboxylates, including, for example, polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, polymaleic acid, polyfumaric acid, copolymers of acrylic and itaconic acid, phosphino polycarboxylate, acid or salt forms thereof, mixtures thereof, and the like.

Further, unlike conventional equilibrium based peroxycarboxylic acid compositions, the present compositions can also be free of, or substantially free of surfactants. This is especially advantageous for compositions incorporating C5 to C18 peroxycarboxylic acids. That is, under perhydrolysis conditions, the C5-C18 peroxycarboxylic acid anions generated are water soluble. If the anions (e.g. peroxycarboxylic acid-forming compositions) are acidified for end use applications, the concentrations of peroxycarboxylic acids are below the water solubility limit of the peroxycarboxylic acids. Thus, couplers are not needed to couple the peroxycarboxylic acids in solution.

Additional Functional Ingredients

The compositions may also include additional functional ingredients. Additional functional ingredients suitable for use in the present compositions include, but are not limited to, acidulants, hydrotropes, dispersants, antimicrobial agents, optical tracers, solidification agent, aesthetic enhancing agent (i.e., colorant (e.g., pigment), odorant, or perfume), among any number of constituents which can be added to the composition. For example, suitable functional ingredients for various embodiments of the invention are hydrotropes, which may be desired for producing clear compositions or dispersants which are more efficient in producing homogeneous dispersions. Such adjuvants can be preformulated with the present compositions or added to the compositions after formation, but prior to use. The compositions can also contain any number of other constituents as necessitated by the application, which are known and which can facilitate the activity of the present compositions.

Acidulant

In an embodiment, the present compositions can include an acidulant. The acidulant can be added to the compositions after the formation of the percarboxylic acid. That is, an acidulant can be added to the peroxycarboxylic acid concentrate to form an acidified use solution. The acidulant can be effective to form a use composition with pH of about 1 or less. The acidulant can be effective to form a use composition with pH of about 8, about 8 or less, about 7, about 7 or less, about 6, about 6 or less, about 5, about 5 or less, or the like. In some embodiments, the acidulant is present at an amount effective to form a use solution with a pH of about 6 to about 8, about 1 to about 8, or about 1 to about 5. In a further embodiment, the acidulant may be added to a semi-diluted reaction solution to produce meta-stable peracid composition.

Any suitable acid can be included in the compositions as an acidulant. In an embodiment the acidulant is an acid or an aqueous acidic solution. In an embodiment, the acidulant includes an inorganic acid. In some embodiments, the acidulant is a strong mineral acid. Suitable inorganic acids include, but are not limited to, sulfuric acid, sodium bisulfate, phosphoric acid, nitric acid, hydrochloric acid. In some embodiments, the acidulant includes an organic acid. Suitable organic acids include, but are not limited to, methane sulfonic acid, ethane sulfonic acid, propane sulfonic acid, butane sulfonic acid, xylene sulfonic acid, cumene sulfonic acid, benzene sulfonic acid, formic acid, acetic acid, mono, di, or tri-halocarboyxlic acids, picolinic acid, dipicolinic acid, and mixtures thereof. In some embodiments, the compositions of the present invention are free or substantially free of a phosphorous based acid.

In an embodiment, the acidulant includes a carboxylic acid with $pK_a$ less than 5. Suitable carboxylic acids with $pK_a$ less than 5 include acetic acid, hydroxyacetic acid, hydroxypropionic acid, other hydroxycarboxylic acids, mixtures thereof, or the like. Such an acidulant is present at a concentration where it does not act as a solubilizer. In some embodiments, the compositions are free of, or substantially free of a carboxylic acid.

In certain embodiments, the present composition includes about 0.001 to about 50 wt-% acidulant, about 0.001 to about 30 wt-% acidulant, about 1 to about 50 wt-% acidulant, about 1 to about 30 wt-% acidulant, about 2 to about 40 wt-% acidulant, about 2 to about 10 wt-% acidulant, about 3 to about 40 wt-% acidulant, about 5 to about 40 wt-% acidulant, about 5 to about 25 wt-% acidulant, about 10 to about 40 wt-% acidulant, about 10 to about 30 wt-% acidulant, about 15 to about 35 wt-% acidulant, about 15 to about 30 wt-% acidulant, or about 40 to about 60 wt-% acidulant. The composition can include any of these ranges or amounts not modified by about.

Premix Formulations

In an embodiment, the reagents described herein (e.g. at least one ester of a polyhydric alcohol and a carboxylic acid, source of alkalinity, oxidizing agent) may be combined into various premix formulations to reduce the number of raw starting materials required for the methods and compositions and further simplify the methods of the invention. According to such an embodiment the providing of premix formulations ensures consistent and stable delivery of reagents.

Premix formulations suitable for use according to the invention may comprise, consist of and/or consist essentially of at least one ester, an oxidizing agent and mixtures thereof. Premix formulations suitable for use according to the invention may comprise, consist of and/or consist essentially of at least one ester, an oxidizing agent, a solvent and mixtures thereof. Premix formulations suitable for use according to the invention may also comprise, consist of and/or consist essentially of at least one ester, an oxidizing agent, water, solvents, dispersing agents, and mixtures thereof.

As one skilled in the art will ascertain the use of premixes employs additional function ingredients for purpose of stabilizing the premix concentrate for use in the compositions and methods according to the invention. For example, hydrotropes, dispersing agents and/or other solvents may be desirable for maintaining the solubility and stability of a particular concentrated premix. The use of any couplers or dispersing agent (such as a surfactant) within a premix formulation is distinct from the use of surfactants in the conventional generation and storage of peracid chemistries, wherein couplers are critical to establishing and maintaining a stable, clear solution of the generated peracid chemistry.

According to the invention, the use of dispersing agents alone within a concentrated premix formulation does not stabilize the premix composition. Rather the dispersing agents are provided in an amount suitable for providing meta-stable peracid compositions generated from the premix after acidification, before further dilution for application. The most efficient dispersing agents were found to be anionic surfactants, and this type of surfactant is known to have high foaming profile. For applications which involves mechanical actions (e.g. CIP sanitizing), the high foam property of the composition is undesirable. Thus, in addition to economic reason, it is preferred to use a minimum amount of the dispersing agent to achieve a meta-stable peracid composition to meet the application of use requirements.

According to an embodiment of the invention less than about 10 ppm, preferably less than about 9 ppm, less than about 8 ppm, less than about 7 ppm, less than about 6 ppm, less than about 5 ppm, less than about 4 ppm, less than about 3 ppm, less than about 2 ppm, or less than about 1 ppm of a dispersing agent is included in the generated peracid chemistry as a result of the use of a surfactant dispersing agent in a concentrated premix formulation according to the invention. This is distinct from the level of surfactants in use solutions of a traditional peracid chemistry, where the amounts of surfactants are normally in excess of about 50 ppm, in excess of about 60 ppm, in excess of about 70 ppm, in excess of about 80 ppm, in excess of about 90 ppm, or in excess of about 100 ppm.

According to a further embodiment of the invention less than about 2% dispersing agent is present in the premix composition, wherein at least about 5%, about 6%, about 7%, about 8% or about 9% are required to provide the stable, clear solution of a generated peracid chemistry when acidified. This is distinct from the generated peracid chemistry according to the invention wherein a meta stable chemistry is generated. Although not wishing to be limited to a particular theory of mechanism of action of the invention, the generated meta-stable composition is a milky colored composition having stability for at least a few hours.

According to an embodiment of the invention, the use of a solvent (e.g. ethanol) is an efficient way to make a stable premix composition. Solvents suitable for the concentrated premix formulations according to the invention include, for example, organic solvents such as alcohol, ether or ketone. Preferably, the solvent is a water soluble alcohol, such as ethanol, methanol, propanol, isopropanol and/or butanol. As one skilled in the art will ascertain the various isomers of the solvents, including alcohols, are further included within the scope of the solvents suitable for use with the concentrated premix formulations of the invention.

Beneficially, the use of concentrated premix formulation still does not require the use of any chelators and/or stabilizers. As a result, regardless of whether individual reagents or concentrated premix formulations are utilized according to the invention, both the reagents and the peracid compositions generated according to the invention provide sustainable chemistries as a result of the elimination of the use of various stabilizers and/or additional amounts of chemistry required to drive the formation of traditional peracid chemistry. As a result of reduced input of reagents for the compositions according to the invention (e.g. resulting from the use of a non-equilibrium reaction) there is a significantly reduced waste stream (e.g. any reagents and/or percentage of composition not impacting the micro-efficacy of the compositions). Instead the present invention provides increased amounts of post-reaction products (e.g. peracids) with decreased amounts of unreacted reagents. In particular, according to the invention the systems generate higher concentrations of the peroxycarboxylic acid(s) and lower concentrations of hydrogen peroxide (e.g. unreacted reagents) than achieved in equilibrium systems.

In an aspect of the invention, a premix formulation may deliver the ester of a polyhydric alcohol and a carboxylic acid and the oxidizing agent. In one aspect a premix formulation includes an ester of a polyhydric alcohol and a carboxylic acid, an oxidizing agent and a dispersing agent. In another aspect a premix formulation includes an ester of a polyhydric alcohol and a carboxylic acid, an oxidizing agent, a dispersing agent and water.

Suitable dispersing agents for use according to the concentrated premix formulations of the invention include polymers, surface active agents or any compounds which will help to achieve a meta-stable solution after the ester perhydrolysis through the interaction with the peroxy fatty acids generated through perhydrolysis. These may include, for example, sulfonated oleic acids (SOA), 1-octanesulfonic acid (NAS), sodium lauryl sulfonates (SLS) and the like. In another aspect a premix formulation includes an ester of a polyhydric alcohol and a carboxylic acid, an oxidizing agent and a solvent. Ethanol and methanol are examples of suitable solvents for use in stabilizing the concentrated premix formulation according to the invention. The use of the solvent in certain embodiments obviates the use of a dispersing agent for premix stability. However, in alternative embodiments a premix formulation may include an ester of a polyhydric alcohol and a carboxylic acid, an oxidizing agent, a dispersing agent and a solvent. Without wishing to be limited to a particular theory or mechanism of action of the invention, the combined use of a dispersing agent and a solvent within a concentrated premix formulation reduces the overall need for a surfactant dispersing agent in the premix composition.

In still another aspect a concentrated premix formulation includes an oxidizing agent and a dispersing agent.

In certain embodiments, the concentrated premix composition includes about 0.001 to about 90 wt-% ester of the polyhydric alcohol and a carboxylic acid, about 0.1 to about 90 wt-% ester, about 1 to about 75 wt-% ester, about 10 to about 75 wt-% ester, about 25 to about 75 wt-% ester, about 30 to about 70 wt-% ester, or about 30 to about 65 wt-% ester.

In certain embodiments, the concentrated premix composition further includes about 0.001 to about 99 wt-% oxidizing agent, about 0.1 to about 95 wt-% oxidizing agent, about 1 to about 90 wt-% oxidizing agent, about 2.5 to about 60 wt-% oxidizing agent, about 5 to about 50 wt-% oxidizing agent, or about 10 to about 40 wt-% oxidizing agent.

In certain embodiments, the concentrated premix composition further includes about 0.001 to about 50 wt-% dispersing agent, about 0.1 to about 40 wt-% dispersing agent, about 1 to about 30 wt-% dispersing agent, about 5 to about 30 wt-% dispersing agent, about 5 to about 20 wt-% dispersing agent, or about 5 to about 15 wt-% dispersing agent. The amount of dispersing agent is selected to ensure that only enough dispersing agent to obtain a meta-stable solution after perhydrolysis and acidification. Beneficially according to the invention, the premix formulations do not contain sufficient dispersing agent to obtain a one phase premix solution.

In certain embodiments, the concentrated premix composition further includes about 0.001 to about 80 wt-% solvent, about 0.1 to about 40 wt-% solvent, about 1 to about 30 wt-% solvent, about 5 to about 30 wt-% solvent, about 5 to about 20 wt-% solvent, or about 5 to about 15 wt-% solvent. 3 The level of solvent is selected to ensure the sufficient amount to solubilize the ester(s) of polyhydric alcohol in the concentrated premix formulation. As one skilled in the art will ascertain the amount of solvent required for such solubilization will vary depending upon the type and level of ester(s) in the premix composition.

In certain embodiments, the concentrated premix composition further includes about 0.001 to about 90 wt-% water, about 0.1 to about 80 wt-% water, about 1 to about 75 wt-% water, about 5 to about 60 wt-% water, about 10 to about 50 wt-% water, or about 20 to about 40 wt-% water. The premix compositions can include any of these ranges or amounts, including those not modified by about.

The pH of the concentrated premix formulation according to the invention is preferably between 2 and about 10, preferably between about 3 and about 9, and more preferably between about 5 and about 7. Thereafter the pH of the premix formulation is combined with an a source of alkalinity to increase the pH to a pH greater than about 12, greater than about 12.5, or greater than about 13 according to the invention.

Methods of Making Peracid Compositions

In some aspects methods for on-site generation of the peroxycarboxylic acid forming compositions and peroxycarboxylic acid using temperature controls are disclosed. The methods include inputting a user-desired or system-controlled peroxycarboxylic acid forming composition or peroxycarboxylic acid formulation into a control software for on-site generation, wherein the input formulation selects an individual or mixed peroxycarboxylic acid forming composition or peroxycarboxylic acid and corresponding volume or mass for on-site generation.

The methods further comprise, consist of and/or consist essentially of combining at least one ester of a polyhydric alcohol and a C1 to C18 carboxylic acid, a source of alkalinity and an oxidizing agent in a reaction vessel of the system at a pH above at least 12. In some embodiments, the pH of the reaction mixture is greater than about 12. In other embodiments, the reaction mixture is greater than about 12.5, or greater than about 13. The methods include the use of a system that is insensitive to environmental temperatures of the location of the apparatus and/or reagents as set forth according to the various embodiments of the invention disclosed herein. The methods further comprise, consist of and/ or consist essentially of generating a peroxycarboxylic acid forming composition or peroxycarboxylic acid.

In some embodiments a formulation user- or system-controlled input may be put into a control software for an ABF system, wherein the input formulation selects an individual or mixed peroxycarboxylic acid forming composition or peroxycarboxylic acid and the corresponding volume or mass of the chemistry for onsite generation. In further embodiments a user controls the input for the on-site chemistry generation. In further embodiments, a system-controlled input may include, for example, a CIP process, bottle washer, aseptic filler, vegetable wash or rinse sink, $3^{rd}$ sink sanitizing sink, textile bleaching process and combinations thereof.

In some embodiments, the user- or system-input selects either a single or multiple reaction vessel mode for the peroxycarboxylic acid and/or mixed peroxycarboxylic acid or peroxycarboxylic acid forming composition generation. As a result of the reaction vessel mode selected by the input, the addition of the reaction reagents, including at least the esters, source of alkalinity and oxidizing agent, may be added in parallel or sequentially. The reagents can be combined in any suitable manner according to the invention and mixed for an amount of time effective to form the desired percarboxylic acid forming composition or percarboxylic acid concentration.

According to the invention, reagents may be added substantially simultaneously to a single reaction vessel, and mixed for an amount of time effective to form the desired concentration. Alternatively, reagents may be added sequentially to a single reaction vessel or separate reaction vessels. Still further, reagents may be combined from separate reaction vessels into an additional reaction vessel or a reservoir (e.g. dilution tank).

According to an embodiment of the invention, the reagents are mixed in one or more reaction vessels for a period of time sufficient for the perhydrolysis reaction to occur. In some embodiments, the reagents are mixed for about 5 to about 30 minutes. In other embodiments, the reagents are mixed for about 10, about 15, about 20, or about 25 minutes. The mixing may take place using a variety of mixing mechanisms, including for example, an impeller or a mechanical blade mixer, such as a mixer having a variable speed control motor to achieve homogeneous blending of reagents.

In additional preferred embodiments the mix order of reagents are controlled to produce a consistent output of peracid chemistry without any fouling (e.g. precipitation) of the reagents. In one aspect of the invention, the source of alkalinity (e.g. sodium hydroxide or caustic soda) is combined with water (e.g. diluted) prior to the addition of the ester source. As disclosed herein the ester source can further be provided in an ester premix (e.g. ester/peroxide premix).

The concentration of reagents, in addition to mixing order, can further be used to control the production of the percarboxylic acid composition. In a preferred embodiment, the concentration of the source of alkalinity is diluted to produce a consistent output of chemistry without any fouling (e.g. precipitation) of the reagents. In one aspect the concentrated alkaline solution (e.g. NaOH) is diluted with a water source before the ester component is combined with the reagents. Although not intending to be limited according to any theory of the invention and/or mechanism of action, the invention demonstrates superior chemistry generation when a system delivers a source of alkalinity (e.g. NaOH solution) that is no more than about 50%, preferably no more than about 40% on an actives basis before combining with the ester reagent to initiate the peracid production reaction.

According to preferred methods of making the peracid chemistry, an ex-situ ABF generator system using an injection manifold to combine an alkaline source, an ester precursor, a peroxygen source and optionally water for production of a peroxy acid is used. Preferably the alkaline source is caustic soda, wherein the caustic stream feeding the manifold is a diluted source of alkalinity. In an aspect the caustic can be diluted within the manifold to the target concentration of less than about 50% by weight, preferably less than about 40%. In an additional embodiment, the ester is added to the system downstream (e.g. after the addition of the diluted NaOH solution).

In an embodiment, the extent of the ester perhydrolysis reaction is measured using one or more measurement devices. Suitable measurement devices measures one or more reaction kinetics or system operations, including for example fluorescence, weight, flow, capacitive level, pH, oxidation reduction potential, pressure, temperature and combinations thereof, as disclosed herein. According to an embodiment, the measurement devices may be used to determine the need and/or timing to add an acid or aqueous acidic solution to dilute the peroxycarboxylic acid forming composition to form the peroxycarboxylic acid composition. In some embodiments the addition of an acid or aqueous acidic solution decreases the pH of the reaction mixture from greater than about 12 to a neutralized pH of about 1.0 to about 8.0.

In an embodiment of the invention, the peroxycarboxylic acid forming composition is dispensed for use in a cleaning process. According to an embodiment, the peroxycarboxylic acid forming composition may be generated in batches approximately at least about every 15 minutes, preferably about every 10 minutes, and more preferably about every 5 minutes. An acid or aqueous acidic solution may be added to the peroxycarboxylic acid forming composition outside of the system according to the invention.

In an embodiment of the invention, the peroxycarboxylic acid forming composition reaction goes to completion within less than about 30 minutes, preferably within less than about 25 minutes, within less than about 20 minutes, within less than about 15 minutes, within less than about 10 minutes, and most preferably within less than about 5 minutes.

In a further embodiment of the invention, the peroxycarboxylic acid forming composition maintains a peracid concentration within about 10% of its final completion concentration for at least about 1 minute. More preferably, the peroxycarboxylic acid forming composition maintains a peracid concentration within about 10% of its final completion concentration for at least about 2 minutes, for at least about 3 minutes, for at least about 4 minutes, for at least 5 minutes, for at least 10 minutes, for at least 15 minutes, and still more preferably for at least 20 minutes.

Preferably, the ABF system, including the reaction vessels, is cleaned between batches of peroxycarboxylic acid forming compositions. Rinsing of the ABF system is expected to have an impact on yield of the peroxycarboxylic acid forming compositions. According to an embodiment of the invention, the system is rinsed (e.g. feed pump lines flushed) with warm/hot water between batches, and/or at regularly schedules intervals to comply with regulatory requirements (e.g. sanitizing regulations), as one skilled in the art shall ascertain.

A particularly suitable embodiment of the invention forms a mixed percarboxylic acid composition by using more than one ester of a polyhydric alcohol and a C1 to C18 carboxylic acid as starting reagents. For example, in some embodiments, a mixed percarboxylic acid composition including peracetic acid and peroctanoic acid is formed. To form this composition, an ester of a polyhydric alcohol and a C1 carboxylic acid is combined with an ester of a polyhydric alcohol and a C8 carboxylic acid, a source of alkalinity, and an oxidizing agent. When forming a mixed peracid composition, the order of addition can be varied depending on the reaction conditions. For example, in some embodiments, all of the reagents can be combined and mixed in one step. Alternatively, in some embodiments, one of the esters can be added to a reaction vessel, with an oxidizing agent, and a source of alkalinity added sequentially. This mixture can be allowed to react for an effective amount of time, prior to the second ester being added to the reaction mixture. Preparing the mixed percarboxylic acid system in a stepwise manner also allows for control of the reaction temperature. For example, by splitting the perhydrolysis reactions into two steps, the overall temperature of the reaction mixture is lower.

In some aspects of the invention, the order of addition and time for reaction can be varied according to the desired percarboxylic acid composition. That is, the reaction can be controlled so as to favor the reaction conditions for formation of each of the percarboxylic acids individually. For example, if it is known that one of the esters has a kinetically slower perhydrolysis reaction rate, that ester can be added to the reaction vessel first. After an amount of time sufficient to maximize the percarboxylic acid formation of the first ester, the second ester with a kinetically faster perhydrolysis reaction rate can be added to the reaction vessel.

According to additional aspects of the invention, the selected batch size of a desired percarboxylic acid forming composition or percarboxylic acid impacts the reaction kinetics. According to the invention, a user- or system-inputted batch size (i.e. volume) to the ABF system impacts the reaction kinetics. Although not intending to be limited to a particular theory, when generating various batch sizes with the ABF system according to the invention, not all reactions are linearly time-scaled, such that a larger batch size (i.e. hundreds of gallons) may require a different timing sequence than a smaller batch size (i.e. tens of gallons) depending on the reaction kinetics and various mixing parameters. The present invention accommodates the changes in user- or system-inputted batch sizes, such that for different volumes of peracid compositions the time constants for its formulation will vary.

In some aspects, the present disclosure provides methods for forming an antimicrobial and/or disinfecting composition. The methods include providing a mixed peroxycarboxylic acid forming composition. The mixed peroxycarboxylic acid forming composition includes: a first ester of a polyhydric alcohol and a C1 to C18 carboxylic acid, for example a C1 to C4 carboxylic acid; a second ester of a polyhydric alcohol and a C1 to C18 carboxylic acid, for example a C8 to C11 carboxylic acid; a source of alkalinity; and an oxidizing agent. After allowing the reaction mixture to react for a sufficient amount of time, a mixed percarboxylic acid composition is formed. The mixed peroxycarboxylic acid composition is diluted with an acidic aqueous solution. In some embodiments, the mixed peroxycarboxylic acid composition is diluted with an amount of an acidic aqueous solution effective to provide the diluted composition with a pH of about 1.0 to about 8.0.

In other aspects, the present disclosure provides methods for forming an antimicrobial and/or disinfecting composition including a single percarboxylic acid. The methods include providing a peroxycarboxylic acid forming composition. The composition includes: an ester of a polyhydric alcohol and a C1 to C18 carboxylic acid; a source of alkalinity; and an oxidizing agent, wherein said composition has a pH greater than 12. The peroxycarboxylic acid forming composition is then diluted with an acidic aqueous solution. In some embodiments, the diluted acidic peroxycarboxylic acid composition has a pH of about 1.0 to about 8.0.

Any acidic solution can be used to dilute the peroxycarboxylic acid compositions. In an embodiment, the acidulant includes an inorganic acid. Suitable inorganic acids include, but are not limited to, sulfuric acid, sodium bisulfate, phosphoric acid, nitric acid, hydrochloric acid. In some embodiments, the acidulant includes an organic acid. Suitable organic acids include, but are not limited to, methane sulfonic acid, ethane sulfonic acid, propane sulfonic acid, butane sulfonic acid, xylene sulfonic acid, benzene sulfonic acid, formic acid, acetic acid, mono, di, or tri-halocarboyxlic acids, picolinic acid, dipicolinic acid, and mixtures thereof. In some embodiments, the compositions of the present invention are free or substantially free of a phosphorous based acid.

Methods Employing Peracid Compositions

In some aspects, the present disclosure includes methods of using the peroxycarboxylic acid forming compositions disclosed herein. In some aspects, the methods of using the compositions employ a chemistry having a pH of from about 0 to about 5 for various antimicrobial and/or bleaching applications. In other aspects, the methods of using the compositions employ a chemistry having a pH of from about 5 to about 9 for various antimicrobial and/or bleaching applications. In still further aspects, the methods of using the compositions employ a chemistry having a pH of from about 5 to about 14 for various bleaching applications.

Peracid compositions generated according to the embodiments of the invention may be used for a variety of user-identified biocidal and/or anti-microbial purposes. In some aspects, the on-site generated peracid compositions may be employed for antimicrobial and/or bleaching methods of use. In further aspects, the on-site generated peracid compositions may be employed for any sanitizing methods of use. For example, the invention includes a method for reducing a microbial population, a method for reducing the population of a microorganism on skin, a method for treating a disease of skin, a method for reducing an odor, or a method for bleaching. These methods can operate on an object, surface, in a body or stream of water or a gas, or the like, by contacting the object, surface, body, or stream with a peracid composition of the invention. Contacting can include any of numerous methods for applying a composition, such as spraying the composition, immersing the object in the composition, foam or gel treating the object with the composition, wiping the composition or a combination thereof In some aspects, a composition obtained according to the methods and apparatus of the present invention includes an amount of a peracid composition of the present invention effective for killing one or more of the food-borne pathogenic bacteria associated with a food product, including, but not limited to, *Salmonella typhimurium, Salmonella javiana, Campylobacter jejuni, Listeria monocytogenes*, and *Escherichia coli* O157:H7, yeast, and mold. In some embodiments, the compositions obtained according to the methods and apparatus of the present invention include an amount of a peracid composition effective for killing one or more of the pathogenic bacteria associated with a health care surfaces and environments including, but not limited to, *Salmonella typhimurium, Staphylococcus aureus, Salmonella choleraesurus, Pseudomonas aeruginosa, Escherichia coli, mycobacteria*, yeast, and mold. The compositions obtained according to the methods and apparatus of the present invention have activity against a wide variety of microorganisms such as Gram positive (for example, *Listeria monocytogenes* or *Staphylococcus aureus*) and Gram negative (for example, *Escherichia coli* or *Pseudomonas aeruginosa*) bacteria, yeast, molds, bacterial spores, viruses, etc. The compositions obtained according to the methods and apparatus of the present invention, as described above, have activity against a wide variety of human pathogens. The present compositions obtained according to the methods and apparatus of the present invention can kill a wide variety of microorganisms on a food processing surface, on the surface of a food product, in water used for washing or processing of food product, on a health care surface, in a health care environment or the like.

The compositions obtained according to the methods and apparatus of the invention can be used for a variety of domestic or industrial applications, e.g., to reduce microbial or viral populations on a surface or object or in a body or stream of water. The compositions can be applied in a variety of areas including kitchens, bathrooms, factories, hospitals, dental offices, restaurants, clean in place applications, laundry or textile applications and food plants, and can be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials including, for example, ceramic, metal, glass, wood or hard plastic.

Suitable soft surfaces include, for example, paper; filter media, hospital and surgical linens and garments; soft-surface medical or surgical instruments and devices; and soft-surface packaging. Such soft surfaces can be made from a variety of materials including, for example, paper, fiber, woven or nonwoven fabric, soft plastics and elastomers. The compositions obtained according to the methods and apparatus of the invention can also be applied to soft surfaces such as food and skin (e.g., a hand). The present compositions can be employed as a foaming or nonfoaming environmental sanitizer or disinfectant.

The peracid compositions obtained according to the methods and system of the present invention can be included in products such as sterilants, sanitizers, disinfectants, preservatives, deodorizers, antiseptics, fungicides, germicides, sporicides, virucides, detergents, bleaches, hard surface cleaners, hand soaps, waterless hand sanitizers, and pre- or post-surgical scrubs.

The compositions can also be used in veterinary products such as mammalian skin treatments or in products for sanitizing or disinfecting animal enclosures, pens, watering stations, and veterinary treatment areas such as inspection tables and operation rooms. The present compositions can be employed in an antimicrobial foot bath for livestock or people. The compositions can also be employed as an antimicrobial teat dip.

In some aspects, the compositions obtained according to the methods and apparatus of the present invention can be employed for reducing the population of pathogenic microorganisms, such as pathogens of humans, animals, and the like. As one skilled in the art will ascertain, the reducing of pathogenic microorganism populations is particularly suitable for healthcare and institutional applications of use. The compositions exhibit activity against pathogens including fungi, molds, bacteria, spores, and viruses, for example, *S. aureus, E. coli, Streptococci, Legionella, Pseudomonas aeruginosa, mycobacteria, tuberculosis*, phages, or the like. Such pathogens can cause a variety of diseases and disorders, including mastitis or other mammalian milking diseases, *tuberculosis*, and the like. The compositions of the present invention can reduce the population of microorganisms on skin or other external or mucosal surfaces of an animal. In addition, the present compositions can kill pathogenic microorganisms that spread through transfer by water, air, or a surface substrate. The composition need only be applied to the skin, other external or mucosal surfaces of an animal water, air, or surface.

The peracid compositions obtained according to the methods and apparatus of the present invention can also be used on foods and plant species to reduce surface microbial populations; used at manufacturing or processing sites handling such foods and plant species; or used to treat process waters around such sites. For example, the compositions can be used on food transport lines (e.g., as belt sprays); boot and handwash dip-pans; food storage facilities; anti-spoilage air circulation systems; refrigeration and cooler equipment; beverage chillers and warmers, blanchers, cutting boards, third sink areas, and meat chillers or scalding devices. The compositions of the invention can be used to treat produce transport waters such as those found in flumes, pipe transports, cutters, slicers, blanchers, retort systems, washers, and the like. Particular foodstuffs that can be treated with compositions of the invention include, but are not limited to, eggs, meats, seeds, leaves, fruits and vegetables. Particular plant surfaces include both harvested and growing leaves, roots, seeds, skins or shells, stems, stalks, tubers, corms, fruit, and the like. The compositions may also be used to treat animal carcasses to reduce both pathogenic and non-pathogenic microbial levels.

The compositions can also be used to treat waste water where both its antimicrobial function and its oxidant properties can be utilized. Aside from the microbial issues surrounding waste water, it is often rich in malodorous compounds of reduced sulfur, nitrogen or phosphorous. A strong oxidant such as the present invention converts these compounds efficiently to their odor free derivatives e.g. the sulfates, phosphates and amine oxides. These same properties are very useful in the pulp and paper industry where the property of bleaching is also of great utility.

In some aspects, the compositions obtained according to the methods and apparatus of the present invention are useful in the cleaning or sanitizing of containers, processing facilities, or equipment in the food service or food processing industries. The compositions have particular value for use on food packaging materials and equipment, and especially for cold or hot aseptic packaging. Examples of process facilities in which the composition of the invention can be employed include a milk line dairy, a continuous brewing system, food processing lines such as pumpable food systems and beverage lines, etc. Food service wares can be treated with an antimicrobial and/or disinfected with the composition of the invention. For example, the compositions can also be used on or in ware wash machines, dishware, bottle washers, bottle chillers, warmers, third sink washers, cutting areas (e.g., water knives, slicers, cutters and saws), egg washers or the like. Particular treatable surfaces include, but are not limited to, packaging such as cartons, bottles, films and resins; dishware such as glasses, plates, utensils, pots and pans; ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liter, etc.), one gallon milk containers, paper board juice or milk containers, etc.

The compositions can also be used on or in other industrial equipment and in other industrial process streams such as heaters, cooling towers, boilers, retort waters, rinse waters, aseptic packaging wash waters, and the like. The compositions can be used to treat microbes and odors in recreational waters such as in pools, spas, recreational flumes and water slides, fountains, and the like. The composition can also be used in treating microbes found in aqueous systems associated with petroleum or LP gas recovery or fermentation processes and pulp and paper processes and the like.

A filter containing peracid compositions of the present invention can reduce the population of microorganisms in air and liquids. Such a filter can remove water and air-borne pathogens such as Legionella.

The compositions obtained according to the methods and apparatus of the present invention can be employed for reducing the population of microbes, fruit flies, or other insect larva on a drain or other surface.

The compositions of the present invention can also be employed by dipping food processing equipment into the use solution, soaking the equipment for a time sufficient to sanitize or de-stain the equipment, and wiping or draining excess solution off the equipment. The compositions of the present invention may be further employed by spraying or wiping food processing surfaces with the use solution, keeping the surfaces wet for a time sufficient to sanitize the surfaces, and removing excess solution by wiping, draining vertically, vacuuming, etc.

The compositions obtained according to the methods and system of the present invention may also be used in a method of sanitizing hard surfaces such as institutional type equipment, utensils, dishes, health care equipment or tools, and other hard surfaces.

The compositions of the present invention can also be used for laundry or textile applications. The compositions can be employed by rinsing laundry or textile surfaces with the use solution, keeping the surfaces wet for a sufficient time to wash, de-stain, sanitize, bleach and/or rinse the surface.

The peracid compositions can be applied to microbes or to soiled or cleaned surfaces using a variety of methods. These methods can operate on an object, surface, in a body or stream of water or a gas, or the like, by contacting the object, surface, body, or stream with a composition of the invention. Contacting can include any of numerous methods for applying a composition, such as spraying the composition, immersing the object in the composition, rinsing the composition, foam or gel treating the object with the composition, applying with a wipe system or a combination thereof.

A concentrate or use concentration of a peracid composition obtained according to the methods and apparatus of the present invention can be applied to or brought into contact with an object by any conventional method or apparatus for applying an antimicrobial or cleaning composition to an object. For example, the object can be wiped with, sprayed with, foamed on, and/or immersed in the composition, or a use solution made from the composition. The compositions can be sprayed, foamed, or wiped onto a surface; the composition can be caused to flow over the surface, or the surface can be dipped into the composition. Contacting can be manual or by machine. Food processing surfaces, food products, food processing or transport waters, and the like can be treated with liquid, foam, gel, aerosol, gas, wax, solid, or powdered peracid compositions according to the invention, or solutions containing these compositions.

Other hard surface cleaning applications for the compositions include clean-in-place systems (CIP), clean-out-of-place systems (COP), washer-decontaminators, sterilizers, textile laundry machines, ultra and nano-filtration systems and indoor air filters. COP systems can include readily accessible systems including wash tanks, soaking vessels, mop buckets, holding tanks, scrub sinks, vehicle parts washers, non-continuous batch washers and systems, and the like. CIP systems include the internal components of tanks, lines, pumps and other process equipment used for processing typically liquid product streams such as beverages, milk, juices.

A method of sanitizing substantially fixed in-place process facilities includes the following steps. A composition in accordance with various embodiments of the invention is introduced into the process facilities at a temperature in the range of about 4° C. to 60° C. After introduction of the composition, the solution is held in a container or circulated throughout the system for a time sufficient to sanitize the process facilities (e.g., to kill undesirable microorganisms). After the surfaces have been sanitized by means of the present compositions, the solution is drained. Upon completion of the sanitizing step, the system optionally may be rinsed with other materials such as potable water. The compositions can be circulated through the process facilities for 10 minutes or less.

The present methods can include delivering the present composition via air delivery to the clean-in-place or other surfaces such as those inside pipes and tanks This method of air delivery can reduce the volume of solution required.

Methods for Contacting a Food Product

In some aspects, the present invention provides methods for contacting a food product with compositions according to the invention employing any method or apparatus suitable for applying such compositions. For example, in some embodiments, the food product is contacted by the compositions with a spray of the compositions, by immersion in the compositions, by foam or gel treating with the compositions. Contact with a spray, a foam, a gel, or by immersion can be accomplished by a variety of methods known to those of skill in the art for applying antimicrobial agents to food. Contacting the food product can occur in any location in which the food product might be found, such as field, processing site or plant, vehicle, warehouse, store, restaurant, or home. These same methods can also be adapted to apply the compositions of the present invention to other objects.

The present methods require a certain minimal contact time of the compositions with food product for occurrence of significant antimicrobial effect. The contact time can vary with concentration of the use compositions, method of applying the use compositions, temperature of the use compositions, amount of soil on the food product, number of micro-organisms on the food product, type of antimicrobial agent, or the like. The exposure time can be at least about 5 to about 15 seconds. In some embodiments, the exposure time is about 15 to about 30 seconds. In other embodiments, the exposure time is at least about 30 seconds.

In some embodiments, the method for washing a food product employs a pressure spray including compositions of the present invention. During application of the spray solution on the food product, the surface of the food product can be moved with mechanical action, e.g., agitated, rubbed, brushed, etc. Agitation can be by physical scrubbing of the food product, through the action of the spray solution under pressure, through sonication, or by other methods. Agitation increases the efficacy of the spray solution in killing micro-organisms, perhaps due to better exposure of the solution into the crevasses or small colonies containing the micro-organisms. The spray solution, before application, can also be heated to a temperature of about 15 to 20° C., for example, about 20 to 60° C. to increase efficacy. The spray stabilized compositions can be left on the food product for a sufficient amount of time to suitably reduce the population of microorganisms, and then rinsed, drained, or evaporated off the food product.

Application of the material by spray can be accomplished using a manual spray wand application, an automatic spray of food product moving along a production line using multiple spray heads to ensure complete contact, or other spray apparatus. One automatic spray application involves the use of a spray booth. The spray booth substantially confines the sprayed compositions to within the booth. The production line moves the food product through the entryway into the spray booth in which the food product is sprayed on all its exterior surfaces with sprays within the booth. After a complete coverage of the material and drainage of the material from the food product within the booth, the food product can then exit the booth. The spray booth can include steam jets that can be used to apply the stabilized compounds of the invention. These steam jets can be used in combination with cooling water to ensure that the treatment reaching the food product surface is less than 65° C., e.g., less than 60° C. The temperature of the spray on the food product is important to ensure that the food product is not substantially altered (cooked) by the temperature of the spray. The spray pattern can be virtually any useful spray pattern.

Immersing a food product in the liquid compositions of the present invention can be accomplished by any of a variety of methods known to those of skill in the art. For example, the food product can be placed into a tank or bath containing the compositions. Alternatively, the food product can be transported or processed in a flume of the compositions. The washing solution can be agitated to increase the efficacy of the solution and the speed at which the solution reduces micro-organisms accompanying the food product. Agitation can be obtained by conventional methods, including ultrasonics, aeration by bubbling air through the solution, by mechanical methods, such as strainers, paddles, brushes, pump driven liquid jets, or by combinations of these methods. The washing solution can be heated to increase the efficacy of the solution in killing micro-organisms. After the food product has been immersed for a time sufficient for the desired antimicrobial effect, the food product can be removed from the bath or flume and the compositions can be rinsed, drained, or evaporated off the food product.

In other embodiments, a food product can be treated with a foaming version of the compositions of the present invention. The foam can be prepared by mixing foaming surfactants with the washing solution at time of use. The foaming surfactants can be nonionic, anionic or cationic in nature. Examples of useful surfactant types include, but are not limited to the following: alcohol ethoxylates, alcohol ethoxylate carboxylate, amine oxides, alkyl sulfates, alkyl ether sulfate, sulfonates, including, for example, alkyl aryl sulfonates, quaternary ammonium compounds, alkyl sarcosines, betaines and alkyl amides. The foaming surfactant is typically mixed at time of use with the washing solution. Use solution levels of the foaming agents is from about 50 ppm to about 2.0 wt-%. At time of use, compressed air can be injected into the mixture, then applied to the food product surface through a foam application device such as a tank foamer or an aspirated wall mounted foamer.

In some embodiments, a food product can be treated with a thickened or gelled version of the compositions of the present invention. In the thickened or gelled state the washing solution remains in contact with the food product surface for longer periods of time, thus increasing the antimicrobial efficacy. The thickened or gelled solution will also adhere to vertical surfaces. The compositions can be thickened or gelled using existing technologies such as: xanthan gum, polymeric thickeners, cellulose thickeners, or the like. Rod micelle forming systems such as amine oxides and anionic counter ions could also be used. The thickeners or gel forming agents can be used either in the concentrated product or mixing with the washing solution, at time of use. Typical use levels of thickeners or gel agents range from about 100 ppm to about 10 wt-%.

Methods for Beverage, Food, and Pharmaceutical Processing

The compositions of the present invention can be used in the manufacture of beverage, food, and pharmaceutical materials including fruit juice, dairy products, malt beverages, soybean-based products, yogurts, baby foods, bottled water products, teas, cough medicines, drugs, and soft drinks The compositions of the present invention can be used to sanitize, disinfect, act as a sporicide for, or sterilize bottles, pumps, lines, tanks and mixing equipment used in the manufacture of such beverages. Further, the compositions of the present invention can be used in aseptic, cold filling operations in which the interior of the food, beverage, or pharmaceutical container is sanitized or sterilized prior to filling. In such operations, a container can be contacted with the compositions, typically using a spray, dipping, or filling device to intimately contact the inside of the container with the compositions, for a sufficient period of time to reduce microorganism populations within the container. The container can then be emptied of the amount of sanitizer or sterilant used. After emptying, the container can be rinsed with potable water or sterilized water and again emptied. After rinsing, the container can be filled with the beverage, food, or pharmaceutical. The container can then be sealed, capped or closed and then packed for shipment for ultimate sale. The sealed container can be autoclaved or retorted for added microorganism kill.

In food, beverage, or pharmaceutical manufacturing, fungal microorganisms of the genus *Chaetomium* or *Arthrinium*, and spores or bacteria of the genus *Bacillus* spp. can be a significant problem in bottling processes, particularly in cold aseptic bottling processes. The compositions of the present invention can be used for the purpose of controlling or substantially reducing (by more than a 5 $\log_{10}$ reduction) the number of *Chaetomium* or *Arthrinium* or *Bacillus* microorganisms in beverage or food or pharmaceutical bottling lines using cold aseptic bottling techniques.

In such techniques, metallic, aluminum or steel cans can be filled, glass bottles or containers can be filled, or plastic (PET or PBT or PEN) bottles, and the like can be filled using cold aseptic filling techniques. In such processes, the compositions of the invention can be used to sanitize the interior of beverage containers prior to filling with the carbonated (or noncarbonated) beverage. Typical carbonated beverages in this application include, but are not limited to, cola beverages, fruit beverages, ginger ale beverages, root beer beverages, iced tea beverages which may be non-carbonated, and other common beverages considered soft drinks. The compositions of the invention can be used to sanitize both the tanks, lines, pumps, and other equipment used for the manufacture and storage of the soft drink material and also used in the bottling or containers for the beverages. In an embodiment, the compositions are useful for killing both bacterial and fungal microorganisms that can be present on the surfaces of the production equipment and beverage containers.

Methods for Industrial Processing

In some aspects, the invention includes methods of using the peroxycarboxylic acid forming compositions and/or peroxycarboxylic acids to prevent biological fouling in various industrial processes and industries, including oil and gas operations, to control microorganism growth, eliminate microbial contamination, limit or prevent biological fouling in liquid systems, process waters or on the surfaces of equipment that come in contact with such liquid systems. As referred to herein, microbial contamination can occur in various industrial liquid systems including, but not limited to, air-borne contamination, water make-up, process leaks and improperly cleaned equipment. In another aspect, the peroxycarboxylic acid forming compositions and/or peroxycarboxylic acids are used to control the growth of microorganisms in water used in various oil and gas operations. In a further aspect, the compositions are suitable for incorporating into fracturing fluids to control or eliminate microorganisms.

For the various industrial processes disclosed herein, "liquid system" refers to flood waters or an environment within at least one artificial artifact, containing a substantial amount of liquid that is capable of undergoing biological fouling, it includes but is not limited to industrial liquid systems, industrial water systems, liquid process streams, industrial liquid process streams, industrial process water systems, process water applications, process waters, utility waters, water used in manufacturing, water used in industrial services, aqueous liquid streams, liquid streams containing two or more liquid phases, and any combination thereof.

In at least one embodiment this technology would be applicable to any process or utility liquid system where microorganisms are known to grow and are an issue, and biocides are added. Examples of some industrial process water systems where the method of this invention could be applied are in process water applications (flume water, shower water, washers, thermal processing waters, brewing, fermentation, CIP (clean in place), hard surface sanitization, etc.), Ethanol/Biofuels process waters, pretreatment and utility waters (membrane systems, ion-exchange beds), water used in the process/manufacture of paper, ceiling tiles, fiber board, microelectronics, E-coat or electro deposition applications, process cleaning, oil exploration and energy services (completion and work over fluids, drilling additive fluids, fracturing fluids, flood waters, etc.; oil fields—oil and gas wells/flow line, water systems, gas systems, etc.), and in particular water systems where the installed process equipment exhibits lowered compatibility to halogenated biocides.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, patents, and patent applications cited throughout this application are hereby incorporated by reference. The invention is further illustrated by the following examples, which should not be construed as further limiting.

All publications and patent applications in this specification are indicative of the level of ordinary skill in the art to which this invention pertains. All publications and patent applications are herein incorporated by reference to the same extent as if each individual publication or patent application was specifically and individually indicated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

A single peracid chemistry (POOA) was generated using an ABF generator according to an embodiment of the invention using the reagents set forth in Table 1A.

TABLE 1A

| Reagent Formula | | Amt (%) |
|---|---|---|
| ABF POOA | Glycerol Octanoate | 14.67% |
| | $H_2O_2$ 35% | 19.42% |
| | Water | 49.44% |
| | NaOH 50% | 16.47% |

POOA production rates were generated as a function of reagents and generator temperatures. A continuous ABF generator was used wherein both the reagent and reaction vessels temperature were controlled with a heating/cooling water bath as set forth in Table 1B. The results demonstrate the POOA production as a function of time.

TABLE 1B

| 5° C. Rxn | | 20° C. Rxn | | 30° C. Rxn | | 40° C. Rxn | |
|---|---|---|---|---|---|---|---|
| time | % POOA 5° C. | time | % POOA 20° C. | Time | % POOA 30° C. | time | % POOA 40° C. |
| 10 | 2.55 | 1 | 2.07 | 1 | | 1 | 5.19 |
| 20 | 3.45 | 5 | 3.89 | 3 | 4.56 | 3 | 6.23 |
| 30 | 3.90 | 10 | 4.77 | 5 | 5.24 | 5 | 6.06 |
| 40 | 4.20 | 15 | 5.46 | 10 | 6.35 | 7 | 5.36 |
| 50 | 4.20 | 20 | 5.83 | 15 | 6.57 | 10 | 5.40 |
| 60 | 4.50 | 25 | 6.30 | 20 | 6.52 | 15 | 3.38 |
| 70 | 4.72 | 30 | 6.67 | 30 | 6.29 | 20 | 3.82 |
| | | 40 | 6.77 | 45 | 5.60 | | |
| | | 50 | 6.73 | 90 | 4.36 | | |
| | | 70 | 6.61 | | | | |
| | | 90 | 6.36 | | | | |
| | | 160 | 5.66 | | | | |

Figure 3:
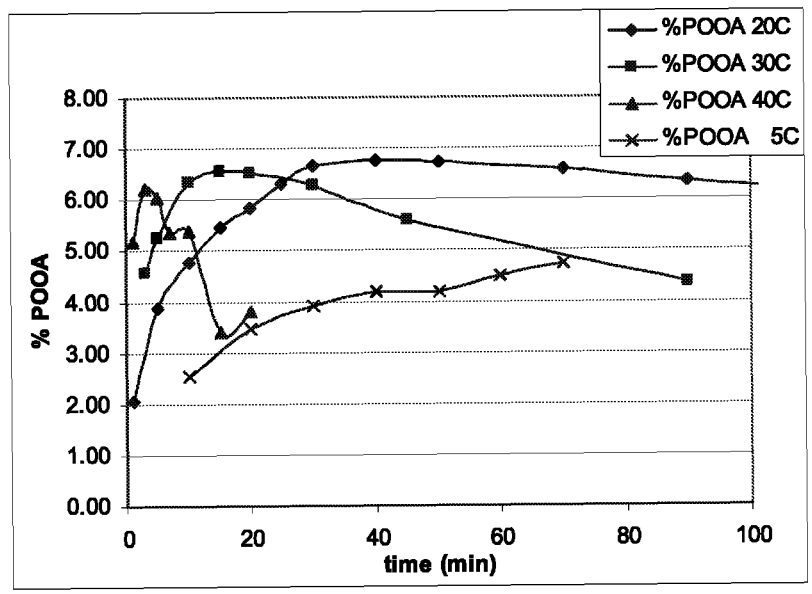
FIG. 3 shows a graph representing POOA concentration over time at various reaction temperatures according to various embodiments of the adjustable biocide formulator apparatus according to the invention.

The results are shown in FIG. 3 (graphical representation of POOA concentration over time at various reaction temperatures). The graph confirms that under different environmental temperatures the concentration of available peracid is widely variable. The variability depends upon the temperature of the generator and temperature of the reactants (e.g. raw starting materials) and of the time point at which the reaction mixture would be used. These results demonstrate the importance of mechanisms for controlling the ex-situ peracid reaction temperature of the reaction vessel or reaction manifold (i.e. regardless of whether batch and/or continuous generation apparatus and/or methods are used according to the invention). The control of temperature impacts the kinetics of the reaction and therefore can be critical to consistency of peracid output according to the invention.

Example 2

Methods of thermal control were analyzed. The reaction rates of a single peracid chemistry (POOA) generated using an ABF generator according to an embodiment of the invention were analyzed. The reagents set forth in Table 2A were used to generate POOA. The test utilized reactants that were stored at either 5° C. or 40° C. (as further shown in Table 2B) to represent the changes in (and ranges of) temperatures one skilled in the art may expect in practice.

TABLE 2A

| Reagent Formula | | Amt (%) |
|---|---|---|
| ABF POOA | Glycerol Octanoate | 9.83% |
| | $H_2O_2$ 35% | 13.02% |
| | Water (21° C.) | 65.90% |
| | NaOH 50% | 11.21% |

The test used a jacket to cover the reaction vessel of the ABF generator to control the temperature of the reagents. In the testing a batch ABF generator was employed (however the same tested methods can be employed for a continuous generator as disclosed pursuant to the invention). The temperature was controlled to 20° C. (~69° F.). In this reaction the glycerol octanoate, peroxide and water reagents (e.g. raw starting materials) were added to the reaction vessel first. Once those ingredients were combined the 50% NaOH was added. For purposes of testing this reaction scheme was utilized as a result of the addition of NaOH both initiating the reaction and causing a large exothermic effect. Both temperature and resultant peracid were monitored in this reaction.

POOA production rates and temperature were monitored as a function of time with reaction vessel temperatures controlled to 20° C., wherein the reagents were stored at either 5° C. or 40° C. The results are shown in Table 2B.

TABLE 2B

| time (min) | temp with 5° C. reagents | temp with 40° C. reagents | POOA @ 5° C. | POOA @ 40° C. |
|---|---|---|---|---|
| 0 | 69 | 84 | 0 | 0 |
| 1 | 80 | 84 | 0.73 | 0.95 |
| 3 | 72 | 73 | 1.36 | 1.58 |
| 5 | 70 | 71 | 1.69 | 1.90 |
| 10 | 69 | 69 | 2.28 | 2.44 |
| 20 | 69 | 69 | 2.80 | 3.04 |
| 30 | 69 | 69 | 3.22 | 3.50 |
| 45 | 69 | 69 | 3.72 | 3.98 |
| 60 | 69 | 69 | 4.02 | 4.24 |
| 90 | 69 | 69 | 4.30 | 4.23 |
| 120 | 69 | 69 | 4.03 | 4.00 |
| 180 | 69 | 69 | | 3.57 |

Figure 4:
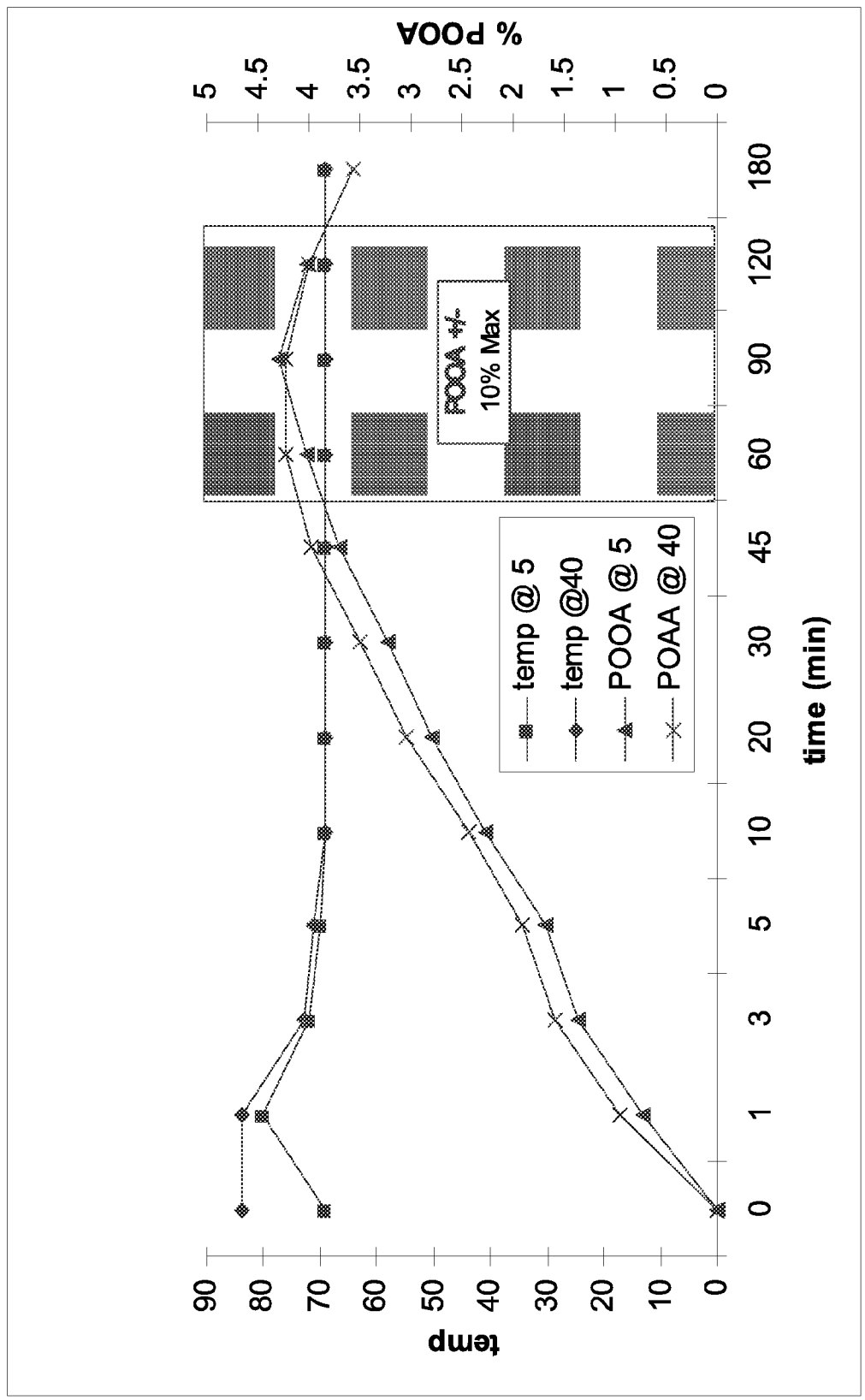
FIG. 4 shows a graph representing POOA production using the adjustable biocide formulator apparatus according to the invention at various temperatures over a period of time.

The results are further shown in the graph of FIG. 4. The identified time period from approximately 50 minutes to 120 minutes (shown in the boxed area of the graph) outlines where the 2 separate reaction mixtures (one with reagents starting at 5° C. and one with reagents starting at 40° C.) achieved maximum percentage POOA generation. These results demonstrate the ability to use temperature control as a means of driving toward consistency in the chemistry output of an ex-situ peracid generator without regard to environmental temperatures.

This example required increased time to achieve maximum generation of the peracid chemistry, notably about 50 minutes to achieve the +/−10% max target for peracid generation. However, as one skilled in the art of chemical reaction kinetics will ascertain, to decrease the time period for achieving maximum peracid generation the temperature of the reaction vessel and/or reaction manifold can be increased.

Example 3

Additional methods of thermal control were analyzed. The thermal control scheme outlined in Example 2 may add cost and/or complexity to an ABF system. As a result, improvements to the various methods for including temperature control for a reaction vessel and/or reaction manifold were analyzed. An alternative was evaluated—heating one or more of the raw starting materials (i.e. reagents) for the ex-situ peracid composition. The heating of reagents as opposed to the reaction vessel and/or reaction manifold was evaluated as a means to control the reaction kinetics in the ABF system.

In this analysis water was selected as the raw starting material that was temperature controlled. Water was selected based on the fact that water tends to be the most abundant reagent in many peracid recipes according to the invention. In addition, the heating of water can be easily and inexpensively achieved as one skilled in the art will appreciate.

The reagents set forth in Table 3A were used to generate POOA.

TABLE 3A

| Reagent Formula | | Amt (%) |
|---|---|---|
| ABF POOA | Glycerol Octanoate | 9.83% |
| | $H_2O_2$ 35% | 13.02% |
| | Water | 65.90% |
| | NaOH 50% | 11.21% |

Table 3B shows the POOA production rates and temperature as a function of time with reagent temperatures controlled to variable temperatures −5° C. and 40° C., as opposed to temperature control of the reaction vessel and/or reaction manifold. The results are shown in Table 3B.

TABLE 3B

| time (min) | POOA 5° C. reagents | POOA 40° C. reagents | Rxn Temp 5° C. reagents | Rxn Temp 40° C. reagents |
|---|---|---|---|---|
| 0 | 0 | 0 | 89 | 94 |
| 1 | 1.26 | 1.65 | 109 | 117 |
| 3 | 2.30 | 2.68 | 106 | 112 |
| 5 | 2.82 | 3.16 | 103 | 108 |
| 10 | 3.56 | 3.65 | 96 | 100 |
| 15 | 3.70 | 3.87 | 85 | 94 |
| 20 | 3.83 | 3.83 | 87 | 89 |
| 30 | 3.92 | 3.76 | 80 | 81 |
| 45 | 3.90 | 3.63 | 74 | 75 |
| 60 | 3.80 | 3.52 | 72 | 72 |
| 90 | 3.62 | | 72 | |

Figure 5:
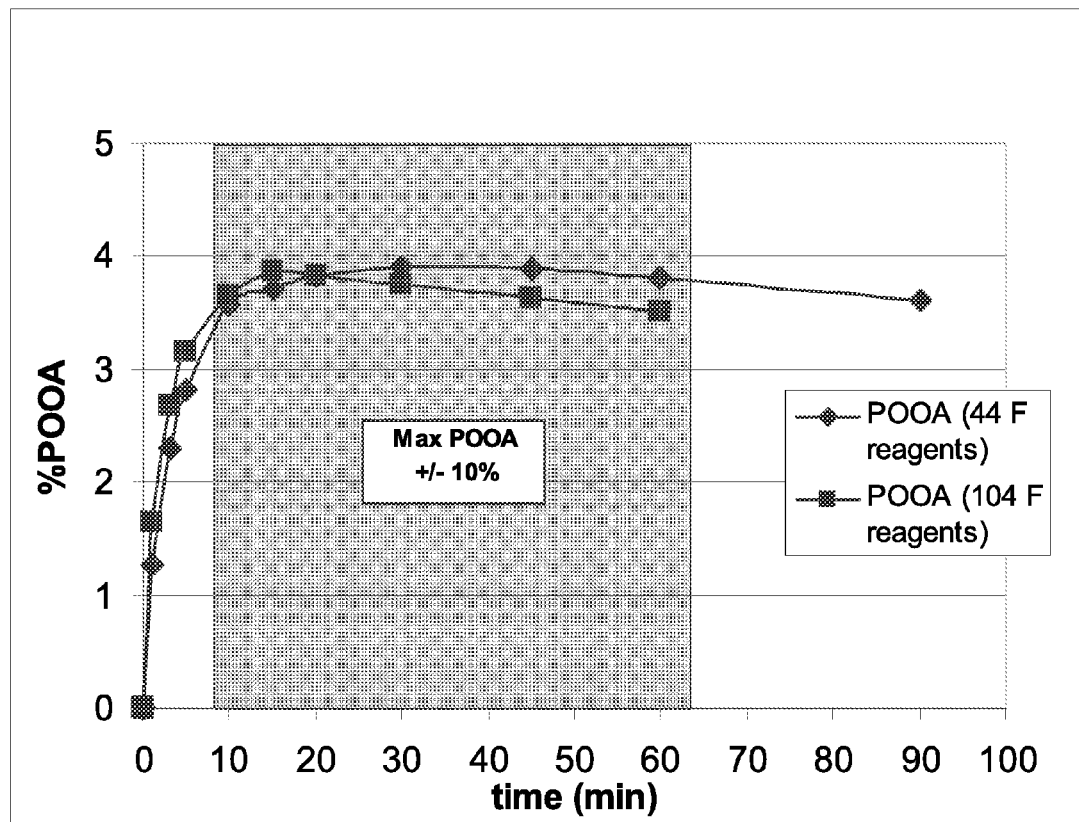
FIG. 5 shows a graph representing POOA production and temperature as a function of time according to various embodiments of the invention.

The results are further shown in the graph of FIG. 5. The results demonstrate the potential to use a heated water source to produce reaction kinetic rates in in ex-situ peracid generator through the use of a heated water source with no other temperature control in the ABF system.

Example 4

Examples 1-3 highlight the importance of using warm water to control reaction rate and stability. Example 4 in contrast outlines an situation where a cooler temperature is preferred to both control reaction rate and stabilize the peracid that is formed.

The reagents set forth in Table 4A were used to generate POAA in a bench top experiment @ ambient environmental temperatures ~70° F. (~21° C.)

TABLE 4A

| Reagent Formula | | Amt (%) |
|---|---|---|
| ABF POAA | Triacetin | 6.0% |
| | $H_2O_2$ 50% | 11.2% |
| | Water | 79.8% |
| | NaOH 50% | 3.0% |

Table 4B shows the POAA production rates and temperature as a function of time using water in the reaction that was preheated to 104F (40 C).

TABLE 4B

| Time (min) | Rxn Temp. (degrees F.) 104° F. water | % POAA |
|---|---|---|
| 0 | 96 | |
| 1 | 110 | 2.41 |
| 2 | 112 | 2.25 |
| 3 | 113 | 1.99 |
| 4 | 113 | 1.77 |
| 5 | 113 | 1.58 |
| 10 | 112 | 0.83 |

Table 4C in contrast show the same reaction scheme using 38 F (~3.3C) water

TABLE 4C

| time (min) | Rxn Temp. (degrees F.) 38° F. water | POAA |
|---|---|---|
| 0 | 46 | |
| 1 | 56 | 2.22 |
| 3 | 58 | 2.49 |
| 5 | 60 | 2.52 |
| 10 | 64 | 2.44 |
| 15 | 67 | 2.36 |

The key difference in these reactions is not in yield, as both compositions develop a maximum concentration of ~2.5% POAA. The critical difference comes down to the stability of the resultant reaction and the ability to maintain a +/−10% max POAA window with the use of cooler than ambient water in this reaction scheme.

The inventions being thus described, it will be obvious that the same may be varied in many ways. Such variations are not to be regarded as a departure from the spirit and scope of the inventions and all such modifications are intended to be included within the scope of the following claims.

The invention claimed is:

1. A method for on-site, temperature controlled peroxycarboxylic acid forming composition generation or peroxycarboxylic acid generation comprising:
   inputting a user-desired or system-controlled peroxycarboxylic acid forming composition or peroxycarboxylic acid formulation into a control software for on-site generation of said peroxycarboxylic acid forming composition or peroxycarboxylic acid formulation, wherein said input formulation selects an individual or mixed peroxycarboxylic acid forming composition or peroxycarboxylic acid and corresponding volume or mass for on-site generation; and
   combining one or more esters of a polyhydric alcohol and a C1 to C18 carboxylic acid, a source of alkalinity and an oxidizing agent at alkaline pH in an adjustable biocide formulator or generator system at a pH above at least 12, wherein said system is an apparatus that is insensitive to environmental temperatures of the location of the apparatus and/or reagents comprising a reaction vessel, a series of feed pumps, an outlet for dosing a peroxycarboxylic acid forming composition from said reaction vessel and a controller for a user- or system-inputted selection device; and generating a peroxycarboxylic acid forming composition or peroxycarboxylic acid formulation;

wherein said temperature insensitivity to the environmental temperatures of the location of the apparatus and/or reagents is controlled by a control mechanism for maintaining a controlled temperature of said reaction vessel and/or one or more reagents;

wherein said control mechanism adjusts the temperature of said reaction vessel and supply of said reagents to a temperature between about 4.4° C. to about 60° C.;

wherein said feed pumps are in fluid connection with said reaction vessel and supply one or more reagents to produce said peroxycarboxylic acid forming composition in said reaction vessel; and wherein said reaction vessel is in fluid connection with said outlet to dispense said peroxycarboxylic acid forming composition.

2. The method according to claim 1, wherein said temperature is adjusted to between about 21° C. to about 49° C.

3. The method according to claim 1, wherein the source of alkalinity is sodium hydroxide, and wherein said sodium hydroxide is provided to said reaction vessel prior to the addition of said ester in a diluted solution.

4. The method according to claim 1, wherein the peroxycarboxylic acid forming composition reaction goes to completion within less than about 30 minutes.

5. The method according to claim 1, wherein the peroxycarboxylic acid forming composition maintains a peracid concentration within about 10% of its final completion concentration for at least about 1 minute.

6. The method according to claim 1, wherein said temperature control mechanism is selected from the group consisting of external heating or cooling of the reaction vessel, internal heating of the reagents within the reaction vessel, preheating one or more of the reagents, and combinations of the same.

7. The method according to claim 6, wherein said reaction vessel is a flow through reactor or a batch reactor and the heated reagent is water.

8. The method according to claim 1, further comprising timing the addition of said esters in parallel or sequentially for reaction in said reaction vessel.

9. The method according to claim 1, further comprising measuring the extent of said ester perhydrolysis reaction using one or more measurement devices, wherein said measurement device measures one or more reaction kinetics or system operations for said peroxycarboxylic acid generation selected from the group consisting of fluorescence, weight, flow, capacitive level, pH, oxidation reduction potential, pressure, temperature and combinations thereof, and wherein said measurement devices determine when to dilute said peroxycarboxylic acid forming composition with an acid or aqueous acidic solution to form said peroxycarboxylic acid.

10. The method according to claim 1, further comprising providing an acid or aqueous acidic solution to form a peroxycarboxylic acid having a pH of about 0.1 to about 8.0, wherein the neutralization with the acid or aqueous acidic solution takes place when the concentration of peracid is within about 10% of its final concentration.

11. The method according to claim 1, further comprising dispensing said peroxycarboxylic acid forming composition for use in a cleaning process, wherein said composition is dispensed from said reaction vessel when the concentration of peracid is within about 10% of its final concentration.

* * * * *